United States Patent
Johnston

(10) Patent No.: US 12,171,630 B2
(45) Date of Patent: Dec. 24, 2024

(54) DENTAL EVACUATION TIP WITH MOUNT FOR DENTAL MOUTH MIRROR

(71) Applicant: Thad Pierce Johnston, Gastonia, NC (US)

(72) Inventor: Thad Pierce Johnston, Gastonia, NC (US)

(*) Notice: Subject to any disclaimer, the term of this patent is extended or adjusted under 35 U.S.C. 154(b) by 77 days.

(21) Appl. No.: 17/924,463

(22) PCT Filed: May 13, 2021

(86) PCT No.: PCT/US2021/032191
§ 371 (c)(1),
(2) Date: Nov. 10, 2022

(87) PCT Pub. No.: WO2021/231696
PCT Pub. Date: Nov. 18, 2021

(65) Prior Publication Data
US 2023/0190431 A1     Jun. 22, 2023

Related U.S. Application Data

(60) Provisional application No. 63/075,526, filed on Sep. 8, 2020, provisional application No. 63/043,914, filed
(Continued)

(51) Int. Cl.
*A61C 17/08* (2006.01)
*A61C 17/06* (2006.01)

(52) U.S. Cl.
CPC ............ *A61C 17/088* (2019.05); *A61C 17/08* (2019.05)

(58) Field of Classification Search
CPC ..... A61C 17/08; A61C 17/084; A61C 17/088; A61C 17/092
See application file for complete search history.

(56) References Cited

U.S. PATENT DOCUMENTS 2,603,870 A * 7/1952 Nordin .................. A61C 17/08
433/93
2,809,430 A    10/1957 Barber
(Continued)

FOREIGN PATENT DOCUMENTS

AU      2005203826 B2    7/2005
CA         2332665 A1    7/2002
(Continued)

OTHER PUBLICATIONS

International Search Report and Written Opinion in counterpart International Application No. PCT/US21/32191, mailed Sep. 9, 2021, pp. 1-14.
(Continued)

*Primary Examiner* — Ralph A Lewis
(74) *Attorney, Agent, or Firm* — Additon, Pendleton & Witherspoon, P.A.

(57) ABSTRACT

A dental evacuation tip has a body defining an interior passageway extending along a length of the body, and proximal and distal openings to the interior passageway. The proximal and distal openings are spaced apart from one another along the length of the body. The dental evacuation tip is configured so that a mirror apparatus can be removably connected to the dental evacuation tip so that at least a portion of a rod of the mirror apparatus is positioned in the interior passageway and a mirror of the mirror apparatus is proximate the distal opening.

20 Claims, 20 Drawing Sheets

Related U.S. Application Data on Jun. 25, 2020, provisional application No. 63/034,661, filed on Jun. 4, 2020, provisional application No. 63/024,786, filed on May 14, 2020.

(56) References Cited

U.S. PATENT DOCUMENTS

| | | |
|---|---|---|
| 3,092,910 A | 6/1963 | Warriner |
| 3,460,255 A * | 8/1969 | Hutson .............. A61C 17/08 433/91 |
| 3,802,081 A * | 4/1974 | Rogers .............. A61C 17/08 433/93 |
| 3,928,916 A | 12/1975 | Hansson |
| 4,521,185 A * | 6/1985 | Cohen .............. A61C 17/08 433/93 |
| 4,629,425 A | 12/1986 | Detsch |
| 5,165,891 A | 11/1992 | Young et al. |
| 5,230,622 A | 7/1993 | Brossoit |
| 5,443,729 A | 8/1995 | Sly et al. |
| 5,608,472 A | 3/1997 | Szirth et al. |
| 5,932,601 A | 8/1999 | Sohda et al. |
| 6,443,729 B1 | 9/2002 | Watson |
| 6,932,601 B2 | 8/2005 | Frider et al. |
| 7,377,780 B2 | 5/2008 | White et al. |
| 7,422,431 B2 | 9/2008 | White et al. |
| 7,553,158 B2 | 6/2009 | Frider et al. |
| 7,913,959 B2 | 3/2011 | White et al. |
| 8,133,052 B1 | 3/2012 | Emmons |
| 8,231,384 B2 | 7/2012 | Sidhu et al. |
| 8,608,472 B2 | 12/2013 | Clasen et al. |
| 9,532,857 B2 | 1/2017 | Ronto |
| D827,140 S | 8/2018 | Caesar |
| 10,709,532 B2 | 7/2020 | Roshkovan |
| 10,945,595 B2 | 3/2021 | Tavor et al. |
| 11,324,397 B2 | 5/2022 | Clasen et al. |
| 11,369,461 B2 | 6/2022 | Clasen et al. |
| 2003/0076605 A1 | 4/2003 | Shohet |
| 2005/0074719 A1 | 4/2005 | Croop et al. |
| 2005/0282103 A1 | 12/2005 | Kwong et al. |
| 2007/0122765 A1 | 5/2007 | Nyman |
| 2009/0017415 A1 | 1/2009 | Cornelius |
| 2010/0021860 A1 | 1/2010 | Christman et al. |
| 2012/0021373 A1 | 1/2012 | Moreno |
| 2012/0034573 A1 | 2/2012 | Erdmann et al. |
| 2015/0374220 A1 | 12/2015 | Hartog |
| 2016/0345815 A1 | 12/2016 | Chen et al. |
| 2018/0168441 A1 | 6/2018 | Tavor et al. |
| 2018/0263484 A1 | 9/2018 | Watson et al. |
| 2019/0298163 A1 | 10/2019 | Tavor et al. |
| 2019/0336255 A1 | 11/2019 | Clasen et al. |
| 2019/0343378 A1 | 11/2019 | Clasen et al. |
| 2020/0038156 A1 | 2/2020 | Clasen et al. |
| 2024/0164881 A1 | 5/2024 | Stango et al. |

FOREIGN PATENT DOCUMENTS

| | | |
|---|---|---|
| CA | 2552777 A1 | 7/2005 |
| CA | 2988685 A1 | 12/2016 |
| CA | 3037867 A1 | 4/2018 |
| CA | 3046534 A1 | 7/2018 |
| CA | 3046536 A1 | 7/2018 |
| CN | 2424740 Y | 3/2001 |
| CN | 1310985 A | 9/2001 |
| CN | 202739967 U | 2/2013 |
| CN | 203379101 U | 1/2014 |
| CN | 106264431 A | 1/2017 |
| CN | 108024702 A | 5/2018 |
| DE | 151690 A1 | 11/1981 |
| DE | 19505603 A1 | 8/1996 |
| DE | 202004018497 U | 2/2005 |
| DE | 202008005491 U1 | 8/2008 |
| DE | 202008011387 U1 | 11/2008 |
| DE | 102012100119 B3 | 12/2012 |
| EP | 1567047 A1 | 8/2005 |
| EP | 1706059 A1 | 10/2006 |
| EP | 2008631 A1 | 12/2008 |
| EP | 2197335 A1 | 6/2010 |
| EP | 2802286 B1 | 11/2014 |
| EP | 3310245 A1 | 4/2018 |
| EP | 3568055 A1 | 11/2019 |
| EP | 3568056 A1 | 11/2019 |
| EP | 3518823 B1 | 8/2021 |
| FR | 2848097 B1 | 6/2004 |
| FR | 2899786 A1 | 10/2007 |
| IL | 239582 B | 1/2019 |
| JP | 7-017213 U | 3/1995 |
| JP | 10-192309 A | 7/1998 |
| JP | 2000-102551 A | 4/2000 |
| JP | 4505615 A | 6/2005 |
| JP | 3823232 B2 | 9/2006 |
| JP | 2007517554 A | 7/2007 |
| JP | 2010-274082 A | 12/2010 |
| JP | 2017-113328 B | 6/2017 |
| JP | 2019533557 A | 11/2019 |
| JP | 2020508090 A | 3/2020 |
| JP | 2020513926 A | 5/2020 |
| KR | 10-2010-0000194 A | 1/2010 |
| WO | 1997034544 A1 | 9/1997 |
| WO | 02078519 A2 | 10/2002 |
| WO | 2005065573 A1 | 7/2005 |
| WO | 2009/047394 A1 | 4/2009 |
| WO | 2016207876 A1 | 12/2016 |
| WO | 2018060188 A1 | 4/2018 |
| WO | 2018130526 A1 | 7/2018 |
| WO | 2018130529 A1 | 7/2018 |

OTHER PUBLICATIONS

International Preliminary Report on Patentability in counterpart International Application No. PCT/US21/32191, mailed Sep. 22, 2022, pp. 1-5.

International Preliminary Report on Patentability in counterpart International Application No. PCT/US21/32191, mailed Apr. 7, 2022, pp. 1-4.

Hufriedygroup, "High Volume Evacuator (HVE) Tips", Ref. ZET / ZETNV / ZES50 (Mar. 2022) pp. 1.

Hufriedygroup, "MaxVac Plus Combo Tip Evacuators", Ref. ZETMVBL / ZETMVGR / ZETMVPK / ZETMVLV / ZETMVYE / ZETMVP (Mar. 2022) pp. 1.

* cited by examiner

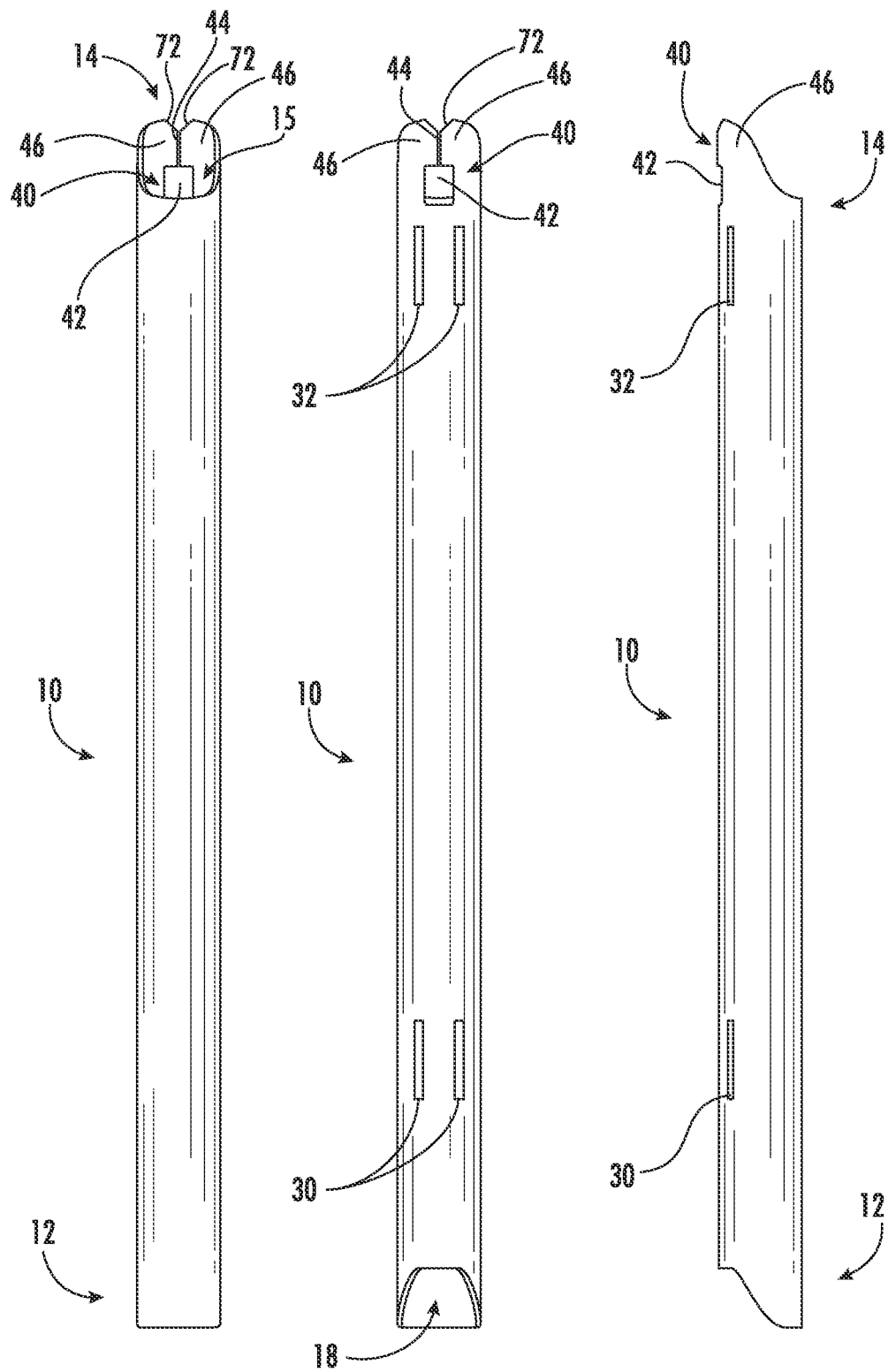

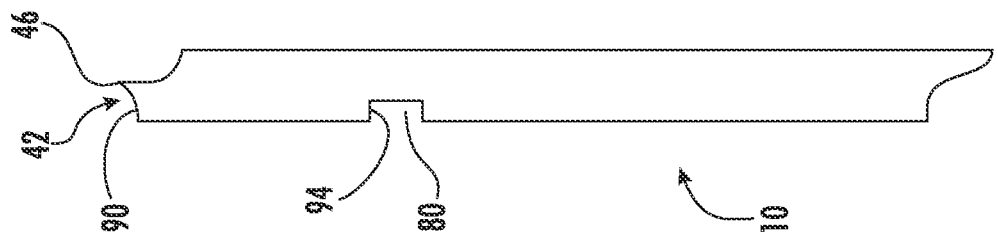
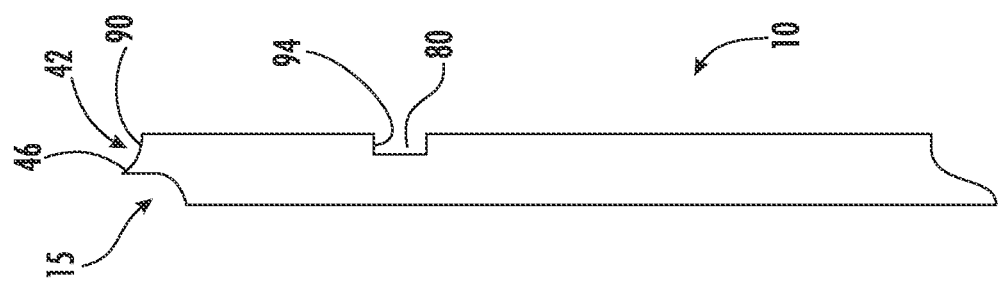
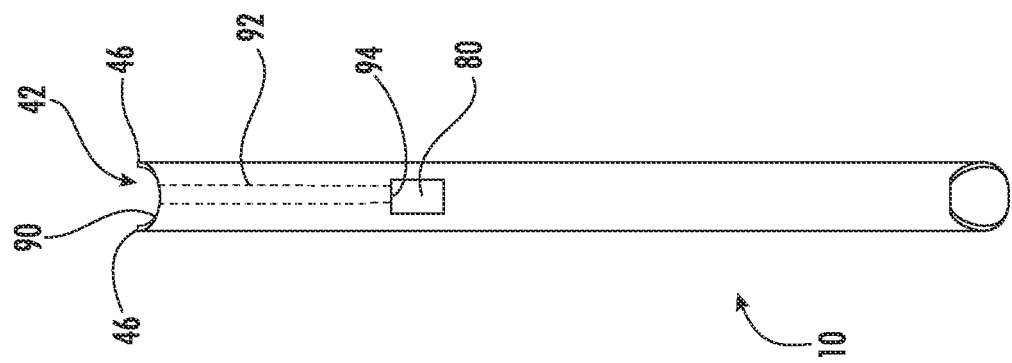
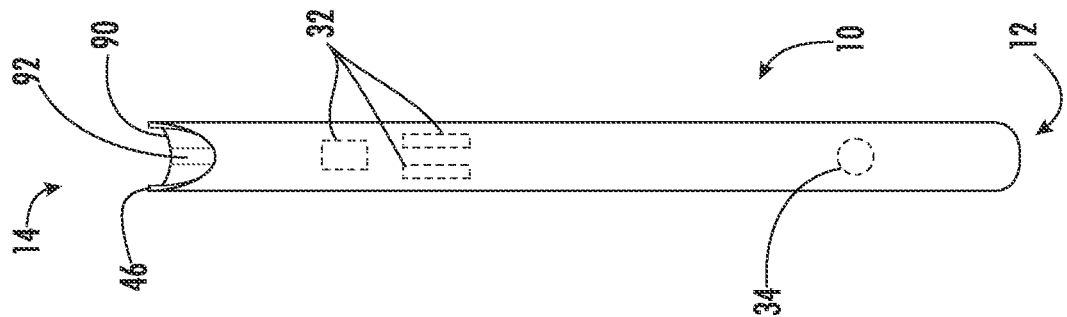

DENTAL EVACUATION TIP WITH MOUNT FOR DENTAL MOUTH MIRROR

CROSS-REFERENCE TO PRIORITY APPLICATIONS

This application claims the benefit of each of U.S. Provisional Patent Application No. 63/024,786 filed May 14, 2020, U.S. Provisional Patent Application No. 63/034,661 filed Jun. 4, 2020, U.S. Provisional Patent Application No. 63/043,914 filed Jun. 25, 2020, and U.S. Provisional Patent Application No. 63/075,526 filed Sep. 8, 2020. Each of the above-referenced applications is incorporated herein by reference in its entirety.

BACKGROUND

Tools exist for facilitating high-volume evacuation (HVE) of aerosols from a dental patient's mouth, but there is a continuing desire for improved dental tools and systems that provide enhanced properties.

SUMMARY

An aspect of this disclosure is the provision of a suction tube that may be used in dentistry, wherein the tube can include at least one mount for a dental mouth mirror apparatus, and/or the tube can include one or more intake holes extending along the length of the tube for intaking aerosol and/or for use in adjusting (e.g., for being opened and closed to adjust) the suction force.

The tube and mirror apparatus can be cooperatively configured as a system so that, when the mirror apparatus is mounted to the tube, at least a portion of the mirror apparatus (e.g., the mirror apparatus' stem and/or handle) extends at least partially within the interior of the tube. The interior of the tube is configured to be in fluid communication with a vacuum source (e.g., partial vacuum), and the tube and mirror apparatus are cooperatively configured so that the portion of the mirror apparatus within the interior of the tube does not prevent fluid from flowing through the interior space of the tube.

The tube and mirror apparatus can be cooperatively configured so that the portion of the mirror apparatus within the interior of the tube extends parallel to, or obliquely relative to, the lengthwise axis of the tube.

The tube's mount for the mirror apparatus can include one or more mounting holes or receptacles in the sidewall of the tube that are configured to receive one or more respective portions of the mirror apparatus and/or at least a portion of a fastener.

The foregoing summary provides brief examples and is not exhaustive, and the present invention is not limited to the foregoing examples. The foregoing examples, as well as other examples, are further explained in the following detailed description with reference to accompanying drawings.

BRIEF DESCRIPTION OF DRAWINGS

The drawings may not be drawn to scale and may be schematic. The present invention may be embodied in many different forms and should not be construed as limited to the examples depicted in the drawings.

FIG. 1 is a rear elevation view of a tube configured to be used, for example, as a dental evacuation tip, wherein the tube includes a mount for a dental mouth mirror apparatus, in accordance with a first embodiment of this disclosure.

FIG. 2 is a front elevation view of the evacuation tip or tube of FIG. 1.

FIG. 3 is a right elevation view of the evacuation tip of FIG. 1, wherein a left elevation view of the evacuation tip of FIG. 1 is a mirror image of FIG. 3.

FIGS. 21-24 respectively are front, rear, right, and left elevation views of an evacuation tip, in accordance with a fifth embodiment of this disclosure.

DETAILED DESCRIPTION

Figure 4:
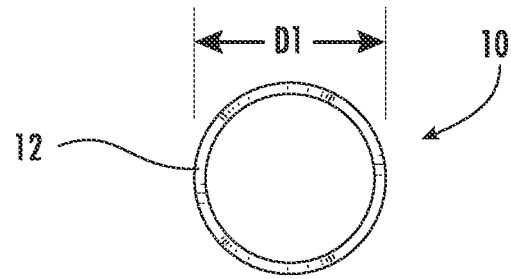
FIG. 4 is a bottom plan view of the evacuation tip of FIG. 1.

Exemplary embodiments are disclosed in the following disclosure. The present invention, however, may be embodied in many different forms and should not be construed as limited to the embodiments set forth herein. For example, features disclosed as part of one embodiment or example can be used in the context of another embodiment or example to yield a further embodiment or example. As another example of the breadth of this disclosure, it is within the scope of this disclosure for one or more of the terms "substantially," "about," "approximately," and/or the like, to qualify each adjective and adverb of the Detailed Description section of this disclosure, as discussed further below.

It is desirable for dental evacuation tips to meet certain air flow requirements to ensure safety and effectiveness. As an example, a non-limiting aspect of this disclosure is the provision of a dental evacuation tip that can securely hold and carry a dental mirror apparatus during use while maintaining effective air flow (e.g., freeing up a hand for the user to perform other tasks at the same time). As a further example, a non-limiting aspect of this disclosure is the provision of such a dental evacuation tip that can be efficiently manufactured and conveniently used with a standard mirror apparatus and/or a standard suction fitting.

FIGS. 1-3 depict a hollow tubular body 10 configured to be capable of being used as a dental evacuation tip (e.g., a suction tube), in accordance with a first embodiment of this disclosure. The body 10, which can be in the form of a tube, pipe, or other suitable conduit that is at least partially close along is sides, typically has opposite proximal and distal ends 12, 14, respectively. The tubular body 10 may have any suitable length extending between the ends 12, 14.

The proximal end 12 is typically conventionally configured to be connected to a conventional fitting (see, e.g., FIG. 10, wherein an outer end portion of a suction fitting 13 is depicted), so that the interior passageway of the tubular body 10 is in fluid communication with the interior passageway of the fitting 13. In use, the fitting 13 is typically in fluid communication with, and upstream from, a vacuum pump, for causing a partial vacuum in the interior of the tube 10, so that air is drawn inwardly through openings of the tube, as discussed further below. The fitting 13 can be a conventional high-speed suction base of a conventional dental evacuation system. A variety of differently configured proximal ends 12 are within the scope of this disclosure. For example, the proximal end 12 can be in different configurations respectively adapted to be connected to different types of fittings 13 (e.g., suction bases).

The distal end 14 is configured to be inserted into a dental patient's mouth so that at least aerosols from the dental patient's mouth can be drawn into the dental evacuation system by way of respective openings to the interior space (e.g., an interior passageway) of the tubular body 10, as discussed further below. The first embodiment tube 10 is also configured to be releasably attached to at least a portion of a conventional (e.g., standard) dental mouth mirror apparatus 16 (see, e.g., FIGS. 6A-10), such as further discussed below. The tube 10 (e.g., dental evacuation tip) can be used with or without the mirror apparatus 16.

In the first embodiment, the tube's end edge at the distal end 14, and the distal end opening 15 (see, e.g., FIGS. 1 and 6B) to the tube's interior, are oblong, substantially oval, and/or the like. That oblong or oval shape can result from the distal end 14 having been cross-sectionally cut from a longer tube at an angle of about 45 degrees (e.g., between about 30 degrees and 60 degrees) relative to the lengthwise axis of the tube 10. The angular value recited in the prior sentence can vary, for example, by plus or minus 5 percent, plus or minus 10 percent, plus or minus 15 percent, plus or minus 20 percent, plus or minus 25 percent, or any subranges or values therebetween. In use, at least aerosols from within the dental patient's mouth can be drawn into the distal end opening 15. The distal end opening 15 can be more generally referred to as a distal opening.

Figure 10:
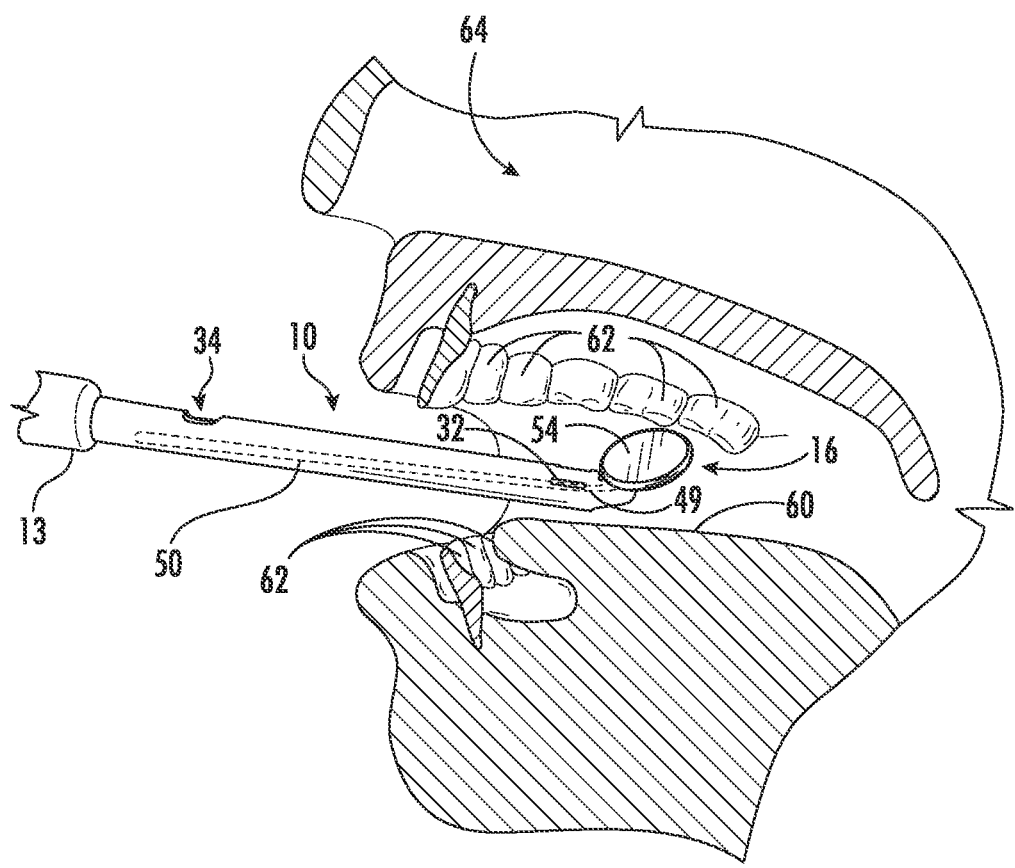
FIG. 10 is a schematic, side, cross-sectional view of a portion of a patient's head, including the patient's open mouth, wherein the combination of FIG. 6B. extends into the mouth, in accordance with an example of a method of the second embodiment.

Referring to FIGS. 2 and 3, similarly to the distal end 14, the tube's end edge at the proximal end 12, and the proximal end opening 18 (FIG. 2) to the tube's interior, may optionally be oblong, substantially oval, and/or the like. The proximal end opening 18 can be more generally referred to as a proximal opening. The tube's proximal end 12 may be inserted into the fitting 13 (FIG. 10). The tube's proximal end 12 can be removably connected to the fitting 13 in any suitable manner. Typically the tube 10 is a disposable item that is separated from the fitting 13 and mirror apparatus 16 (see, e.g., FIGS. 6A-10) after being used with a patient, so that the tube can be discarded, and the fitting and mirror apparatus may be sterilized and reused. Also, the tube 10 and fitting 13 can be used together without there being a mirror apparatus 16 mounted to the tube Further referring to FIGS. 2 and 3, one or more proximal and/or distal intake holes 30, 32 (e.g., ports or other suitably configured holes defining openings to the tube's interior space) can extend through the sidewall of the tube 10. In the first embodiment, the intake holes 30, 32 are in the form of slots, and the lengths of at least some of, or each of, the intake slots 30, 32 can extend along the length of the tube 10. Alternatively, the intake holes 30, 32 can be omitted, more or less numerous, square, round, elliptical, and/or in any other suitable shape, as discussed further below.

In the first embodiment, the one or more distal intake openings or slots 32 can be positioned close enough to the tube's distal end 14 so that, during use, at least aerosols from within the dental patient's mouth can be drawn into the distal intake slots. In contrast, during use, the one or more proximal intake openings or slots 30 can be positioned relatively outwardly from the patient's mouth for intaking at least aerosol that may have exited the patient's mouth, while the distal intake slots 32 and the tube's distal end opening 15 are all positioned in the patient's mouth. The one or more distal intake openings or slots 32 can be configured differently for controlling flow. Similarly, the one or more proximal intake openings or slots 30 can be configured differently and/or be manually obstructed for controlling flow (e.g., by way of a "throttle" or "choke" type effect), as discussed further below.

Because of the above-discussed angular configuration of the tube's distal end 14, the distal end can be described as being tapered, so that there are opposite relatively long and relatively short portions or sides of the tube's distal end. In the embodiments depicted in the drawings, a mount 40 for at least partially receiving and removably holding the mirror apparatus 16 is at least partially defined in the longer side of the distal end 14.

The mount 40 can include a receptacle, opening, mounting hole, or receptacle hole 42 extending through the tube's sidewall. The mount 40 can further include at least one guideway opening 44 extending through the tube's sidewall. The guideway opening 44 can comprise, consist essentially of, or consist of a slit (e.g., guideway slit 44) or a hole (e.g., guideway hole 44) that is wider than a slit. The guideway opening or hole 44 can be elongate and extend between, and be open at each of, the distal end opening 15 and the mounting receptacle or hole 42. As a result, the guideway 44 can be in the form of a guideway slot 44 that at least partially defines opposite tab-portions 46 of the tube 10.

The tab-portions 46 of the mount can be configured to function as resilient mounting or engagement tabs 46 for at least partially mounting the mirror apparatus 16 to the tube 10, such as discussed further below. Differently configured distal end openings 15, mounts 40, receptacles 42, guideways 44, engagement tabs 46, and other features are within the scope of this disclosure. For example, the guideway 44 may be at least one slit that is straight or curved, or the guideway may be a hole 44 that is rounded, curved, rectangular, square, and/or in any other suitable shape. The outer end of the mounting opening or guideway 44 can be tapered, wherein the taper can be defined by one or more beveled edges 72, as discussed further below. In the first embodiment, the receptacle 42 and guideway 44 are differently sized holes that extend through the at least one tube sidewall and are open to one another, so that the receptacle 42 and guideway 44 may be collectively referred to as an irregularly shaped hole, at least one hole, a pair of holes, or the like.

Referring to FIG. 4, the tube 10 can have an inner diameter D1 of about 11.6 millimeters and a sidewall thickness of about 1 millimeter. FIG. 4 is illustrative of the fact that the tubular body 10 of the first embodiment has a circular cross section, although differently configured cross sections are within the scope of this disclosure (e.g., rounded, curved, rectangular, square, and/or any other suitable shape). More generally, differently configured tubes 10 are within the scope of this disclosure. For example, although the tube 10 of the first embodiment extends straightly along its length, the tube can be curved or include at least curve along its length, so that the tube appears to have been bent, or the like.

Figure 5A:
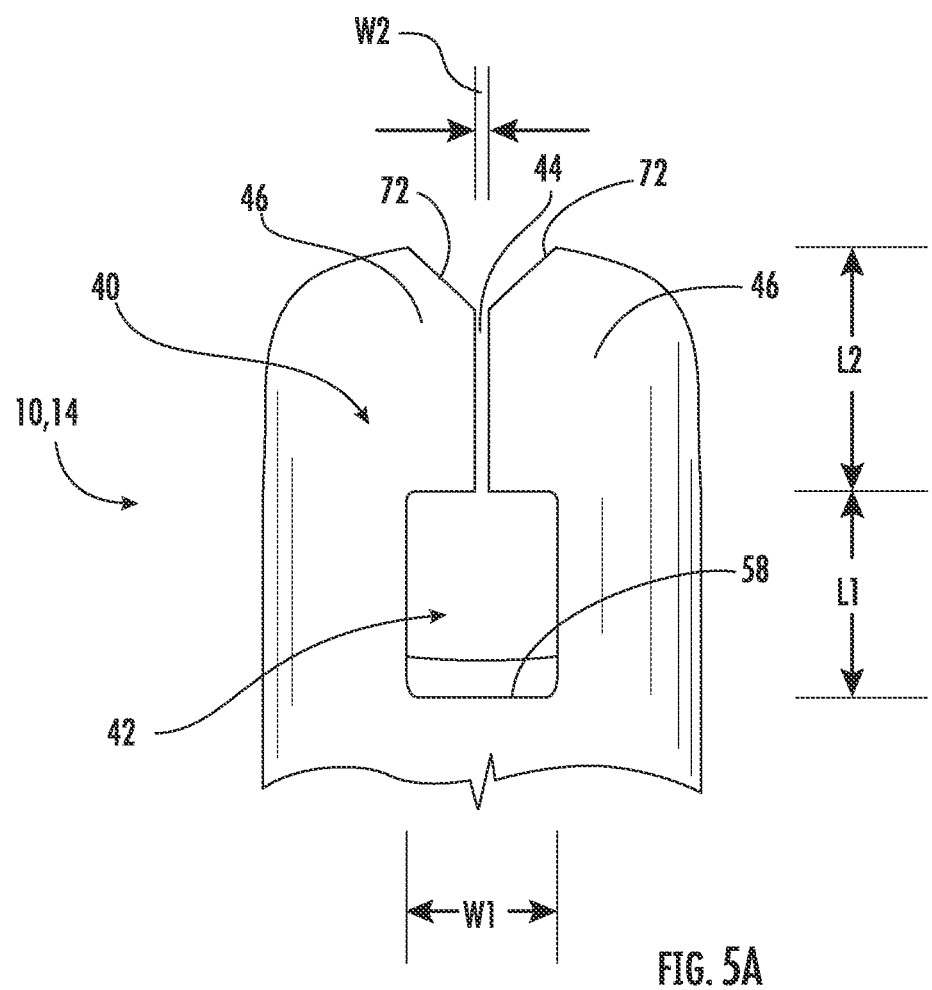
FIG. 5A is a front elevation view of an upper portion of the evacuation tip of FIG. 1.

Referring to FIG. 5A, the mounting hole or receptacle 42 can have a length L1 of about 4 millimeters and a width W1 of about 4.1 millimeters. The mounting or guideway slot 44 can have a length L2 of about 4 millimeters, and a width W2 of about 1 millimeter, about 0.5 millimeters, in a range of from about 0.4 millimeters to about 1.1 millimeters, or any subranges or values therebetween. The values recited in this paragraph can vary, for example, by plus or minus 5 percent, plus or minus 10 percent, plus or minus 15 percent, plus or minus 20 percent, plus or minus 25 percent, plus or minus 50 percent, or any subranges or values therebetween.

Figure 5B:
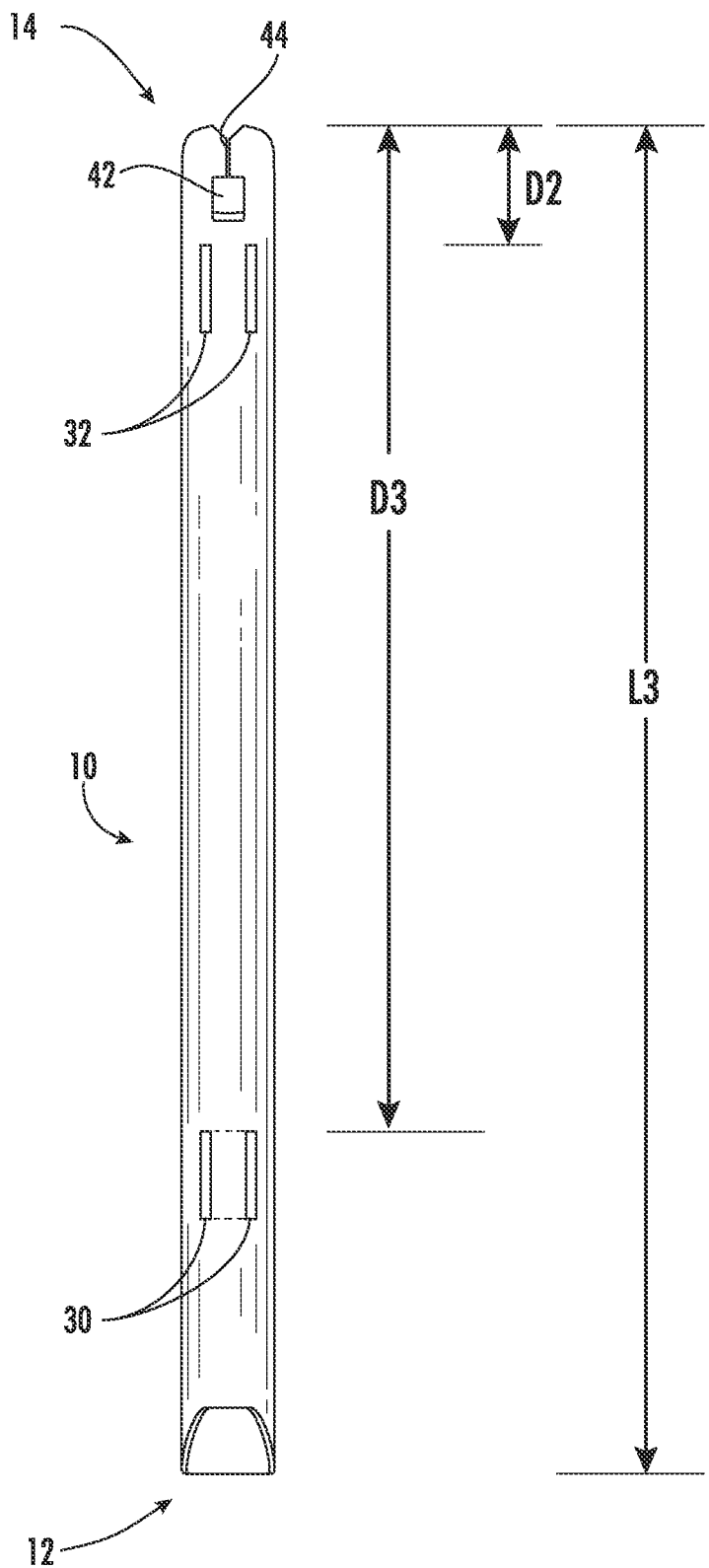
FIG. 5B is another front elevation view of the evacuation tip of FIG. 1, wherein a variation is schematically illustrated with dashed lines.

Referring to FIG. 5B, the tube 10 can have an overall length L3 of about 130 millimeters, about 144 millimeters, about 150 millimeters, about 160 millimeters, in a range of from about 130 millimeters to about 160 millimeters, or any subranges or values therebetween. As another example, the tube 10 can have an overall length L3 of about 144 millimeters, which length can vary, for example, by plus or minus 5 percent, plus or minus 10 percent, plus or minus 15 percent, plus or minus 20 percent, plus or minus 25 percent, plus or minus 50 percent, or any subranges or values therebetween.

At least some of, the majority of, or each of the intake slots 30, 32 can have a length of about 12 millimeters and a width of about 1 millimeter; and each of these dimensions can vary, for example, by plus or minus 5 percent, plus or minus 10 percent, plus or minus 15 percent, plus or minus 20 percent, plus or minus 25 percent, plus or minus 50 percent, or any subranges or values therebetween.

With continued reference to FIG. 5B, the distal intake slots 32 can be a distance D2 of about 14 millimeters from the distal end 14, and this distance can vary, for example, by plus or minus 5 percent, plus or minus 10 percent, plus or minus 15 percent, plus or minus 20 percent, plus or minus 25 percent, plus or minus 50 percent, or any subranges or values therebetween. The proximal intake slots 30 can be a distance D3 of about 84 millimeters from the distal end 14, and this distance can vary, for example, by plus or minus 5 percent, plus or minus 10 percent, plus or minus 15 percent, plus or minus 20 percent, plus or minus 25 percent, plus or minus 50 percent, or any subranges or values therebetween.

The intake openings or slots 30, 32 can be configured differently. For example, FIG. 5B schematically depicts with dashed lines that the proximal intake slots 30 can be connected to one another to form a single intake opening 30.

The first embodiment tube 10 is cylindrical and, thus, has a cylindrical sidewall. Alternatively, the tube 10 may be in the form of any other suitable hollow structural section, for example, a rectangular or elliptical tube, or the like. Accordingly, the tube 10 can be described as including at least one sidewall extending around an interior passageway of the tube 10.

Figure 5C:
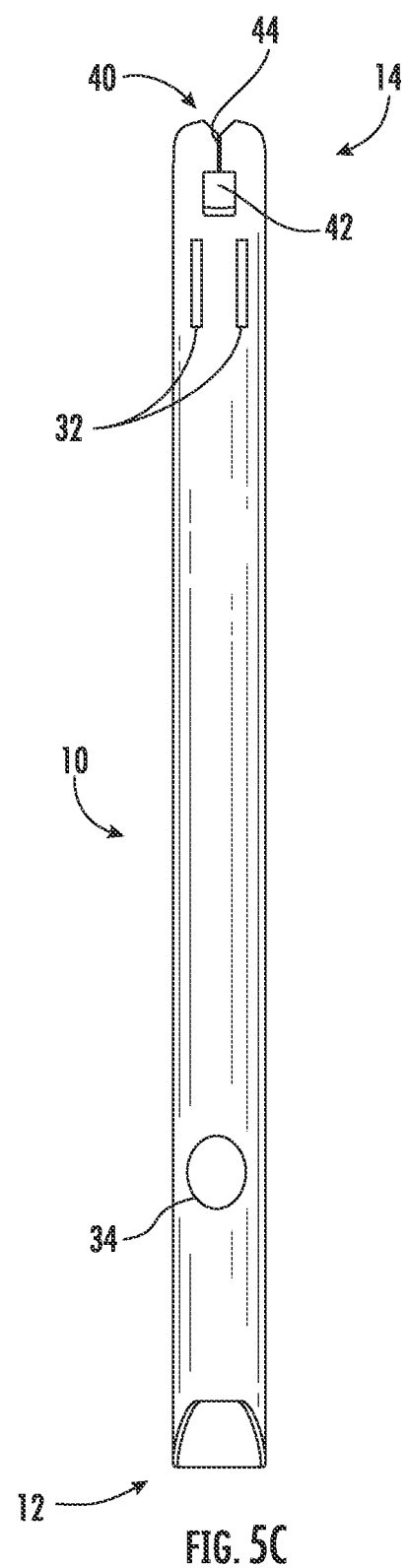
FIG. 5C is a front elevation view of an evacuation tip in accordance with a second embodiment of this disclosure.

Other embodiments are within the scope of this disclosure. For example, FIG. 5C depicts the tube 10 of a second embodiment of this disclosure. The first and second embodiments can be alike, except for variations noted and variations that will be apparent to those of ordinary skill in the art.

Referring to FIGS. 5B and 5C, the proximal intake holes or slots 30 (FIG. 5B) can be omitted and/or replaced by at least one differently configured proximal intake hole 34 (FIG. 5C) extending through the sidewall of the tubular body 10. In the example depicted in FIG. 5C, the at least one proximal intake hole 34 is round and has a diameter in a range of from about 4 millimeters to about 6 millimeters, and each of these distances can vary, for example, by plus or minus 5 percent, plus or minus 10 percent, plus or minus 15 percent, plus or minus 20 percent, plus or minus 25 percent, plus or minus 50 percent, or any subranges or values therebetween. The at least one proximal intake hole 34 can be in any other suitable configuration. For example, the proximal intake hole 34 can be elliptical or rectangular (e.g., with rounded corners) and have a length of about 6 millimeters (e.g., extending along the lengthwise axis of the tube), and a width of about 4 millimeters (e.g., extending perpendicular to the lengthwise axis of the tube), and each of these distances can vary, for example, by plus or minus 5 percent, plus or minus 10 percent, plus or minus 15 percent, plus or minus 20 percent, plus or minus 25 percent, plus or minus 50 percent, or any subranges or values therebetween. The proximal intake hole 34 can be square, round, elliptical, and/or in any other suitable shape. The number, size, shape, and location of the holes 30, 32 can be advantageously varied (e.g., tuned) to adjust flowrates.

In the example depicted in FIGS. 6B-10, the mount 40 is configured for facilitating mounting (e.g., removably connecting) the mirror apparatus 16 to the tube 10. However, the tube 10 can be used with or without the mirror apparatus 16.

Figure 6A:
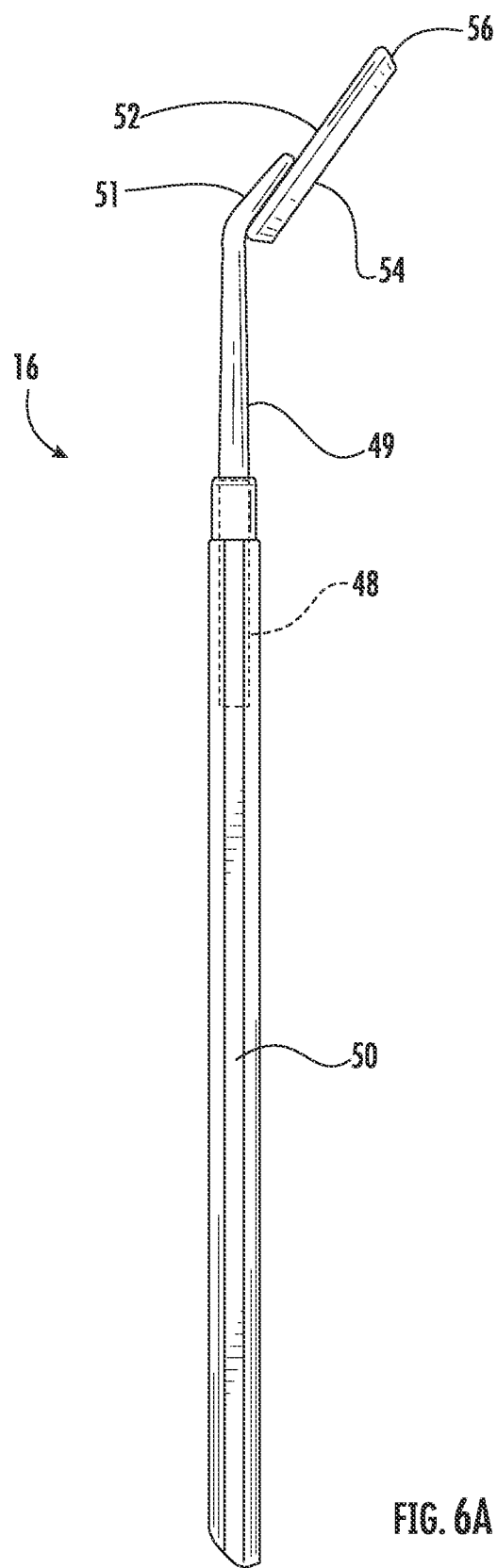
FIG. 6A is a side view of an example of a dental mouth mirror apparatus.

Referring to FIG. 6A, the mirror apparatus 16 can include a handle 50 (e.g., an elongate rod) connected to a head of the mirror apparatus. The handle 50 can be connected to the mirror apparatus' head by way of at least a rod (e.g., stem 49) and/or in any other suitable manner. The stem 49 can comprise, consist essentially of, or consist of an extension, rod, shaft, and/or other suitable structure connected to the mirror apparatus' head. The stem 49 can be fixedly and/or removably attached to the handle 50. For example, the proximal end portion of the stem 49 can be externally threaded, and the distal end portion of the handle can include an internally threaded receptacle for removably receiving the proximal end portion of the stem, and/or the stem and handle can be connected in any other suitable manner. In the example depicted in FIG. 6A, the screw threads of the stem 49 and handle 50 are hidden from view, the screw threads are schematically depicted by dashed lines, and the screw threads are identified by reference numeral 48. In some examples, the handle 50, or the like, can be omitted from the mirror apparatus 16, as discussed further below.

The maximum outer diameter of the handle 50 and the stem 49 are typically smaller than the inner diameter D1 (FIG. 4) of the tube 10, so that the handle and stem do not prevent fluid from flowing through the interior space of the tube 10. Stated differently, the mirror apparatus' extension or body part (e.g., the rod, handle 50 and/or stem 49) within the interior space of the tube 10 only partially obstructs the suction-induced flow through the interior pathway of the tube.

With continued reference to FIG. 6A, the distal end portion of the rod or stem 49 can be in the form of an angled neck or flattened, relative rigid mounting tab 51 that is fixedly connected, by at least one weld or other suitable connecting mechanism, to the rear side of the head of the mirror apparatus. The mounting tab 51 typically is an end portion of the rod or stem 49. The head of the mirror apparatus 16 can include a backplate 52 to which the stem 49, or more specifically to which the mounting neck, mounting lug, or mounting tab portion 51 of the stem, is attached. The mirror apparatus 16 can further include a reflective mirror 54 mounted to the front of the backplate 52 by a bezel 56 and/or in any other suitable manner.

In accordance with an aspect of the first and second embodiments, the mirror apparatus 16 can be characterized as including a head connected to an extension or body part, wherein the mirror apparatus' head comprises, consists essentially of, or consists of the backplate 52, mirror 54, bezel 56, and neck or mounting tab 51, and wherein the mirror apparatus' extension or body part comprises, consists essentially of, or consists of the handle 50 and stem 49. Differently configured mirror apparatus heads and mirror apparatus extensions or body parts are within the scope of this disclosure.

Figure 6B:
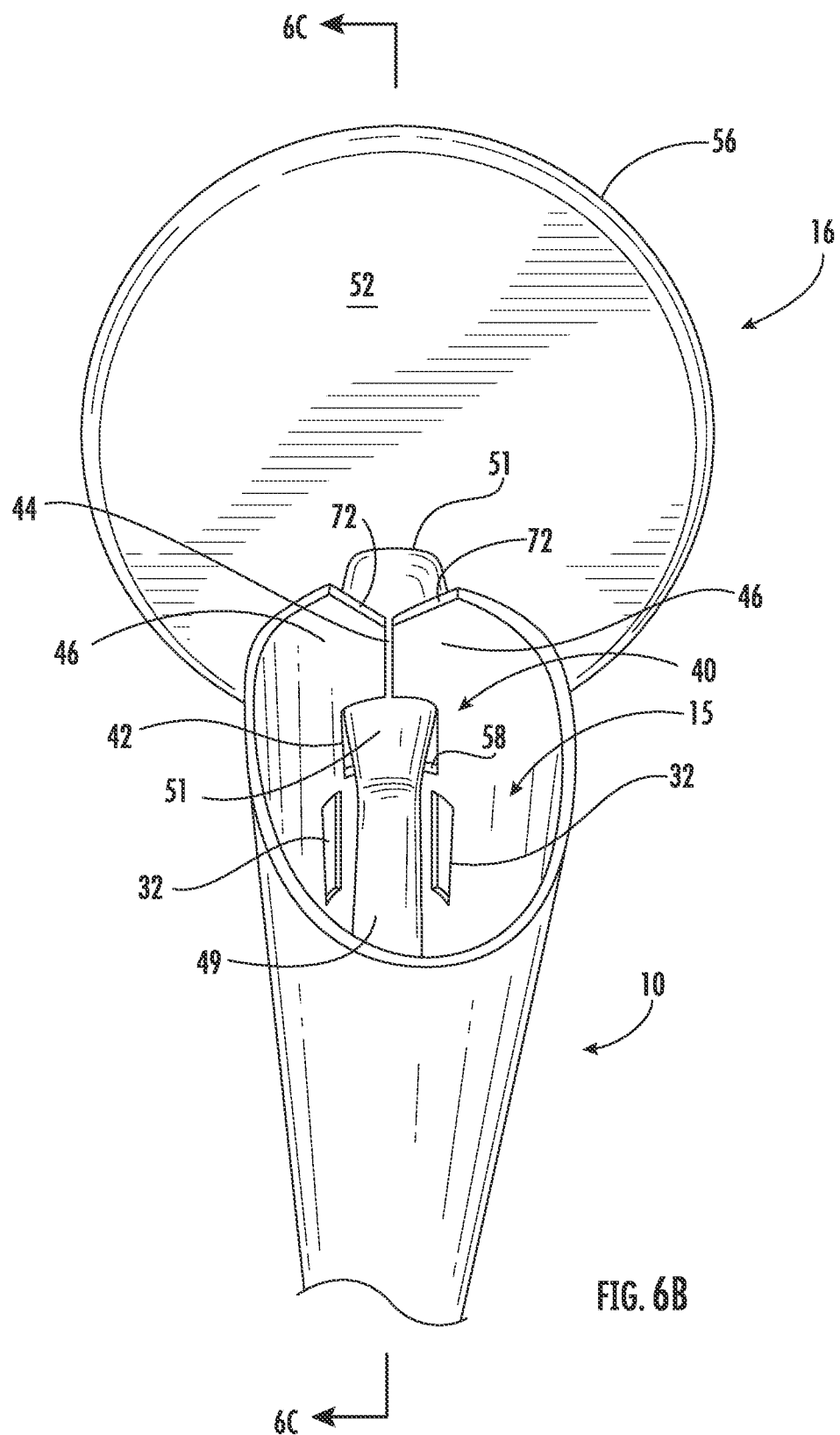
FIG. 6B is a partial, top-rear pictorial view of the mirror apparatus of FIG. 6A mounted to the evacuation tip of FIG. 5C, and FIG. 6B also depicts the mirror apparatus of FIG. 6A mounted to the evacuation tip of FIG. 1, respectively in accordance with the first and second embodiments.
Figure 6C:
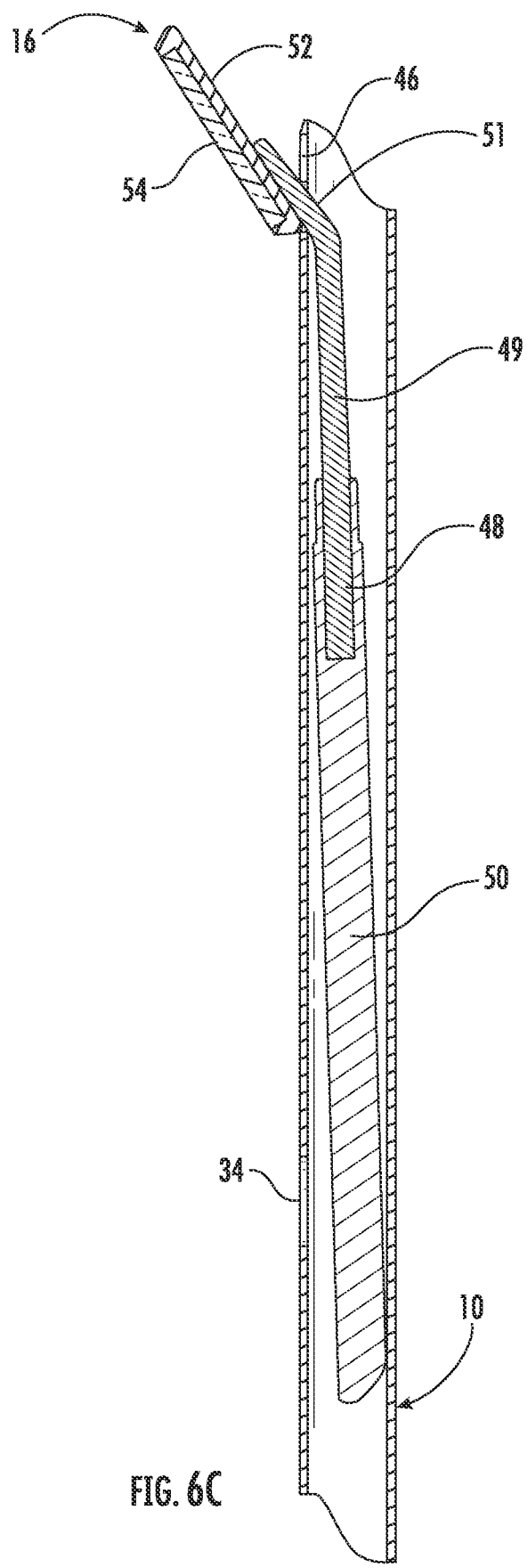
FIG. 6C is a cross-sectional view taken along line 6C-6C of FIG. 6B, in accordance with the second embodiment.

An example of a method of removably mounting the mirror apparatus 16 to the tube 10 of the first and second embodiments is described in the following and can be best understood with reference to FIGS. 6A-9. FIG. 7 is schematic because the distal end portion of the tube 10 that is hidden from view behind the mirror apparatus 16, and the rod(s) 49, 50 of the mirror apparatus that are hidden from view in the tube's interior passageway, are schematically depicted with dashed lines.

Referring to FIGS. 1 and 6A, the proximal end of the mirror apparatus' handle 50 can be inserted through the tube's distal end opening 15 and into the tube's interior space. Then, the handle 50 can be guided farther through the distal end opening 15 and farther into the tube's interior space so that the proximal end of the handle 50 travels in the tube interior space toward the tube's proximal end 12. This relative movement between the tube 10 and mirror apparatus 16 typically continues until the mounting or engagement tabs 46 engage the mirror apparatus' head (e.g., bezel 56, stem 49, neck, mounting tab 51, and/or the like). Then, and as best understood with reference to FIGS. 6B-6F, the stem 49 (e.g., the neck, mounting tab 51, and/or the like) is forced to pass through the guideway, slit, hole, or slot 44 so that the neck, stem 49, mounting tab 51, and/or the like arrives in, and extends through, the receptacle 42.

Alternatively, the handle 50 can be removed from the stem 49 prior to mounting the remainder of the mirror apparatus 16 to the tube 10. Initially, the proximal end of the mirror apparatus' stem 49 can be inserted through the tube's distal end opening 15 and into the tube's interior space. Then, the stem 49 can be guided farther through the distal end opening 15 and farther into the tube's interior space so that the proximal end of the stem 49 travels in the tube interior space toward the tube's proximal end 12.

Figure 6D:
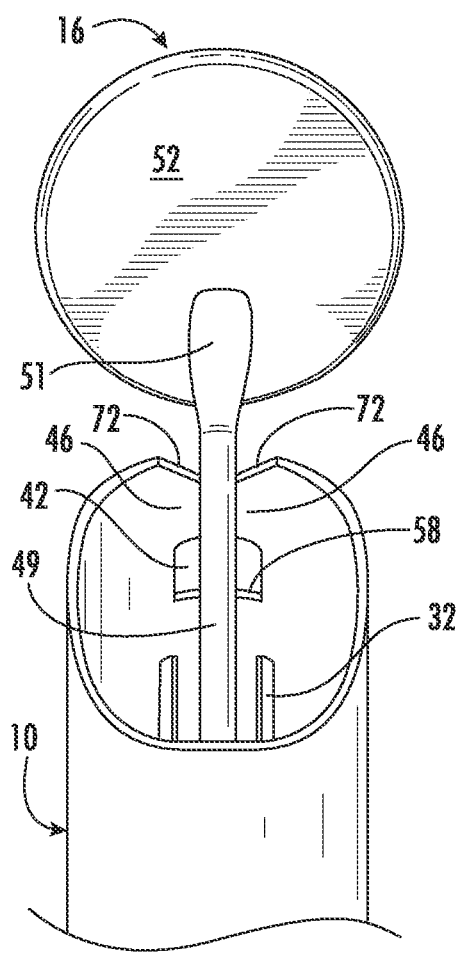
FIGS. 6D-6F are partial views depicting a sequence of steps of mounting the mirror apparatus to the evacuation tip in accordance with the first and second embodiments.
Figure 6E:
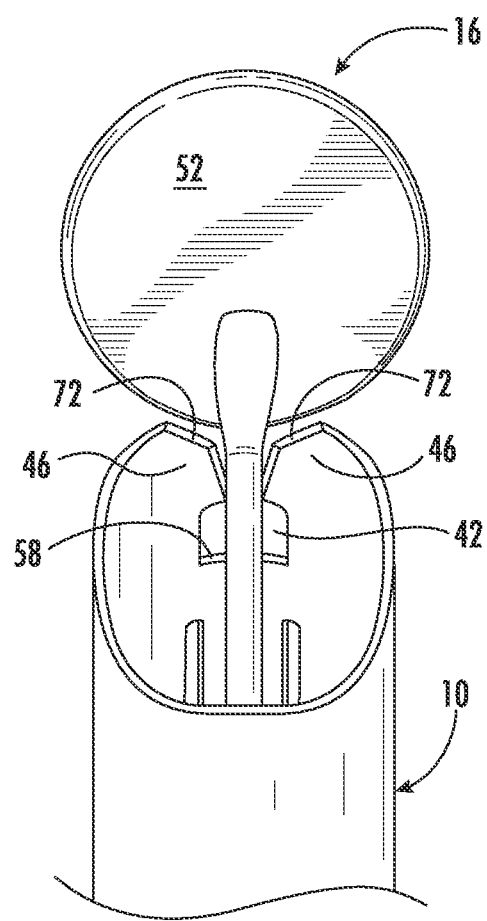
Figure 6F:
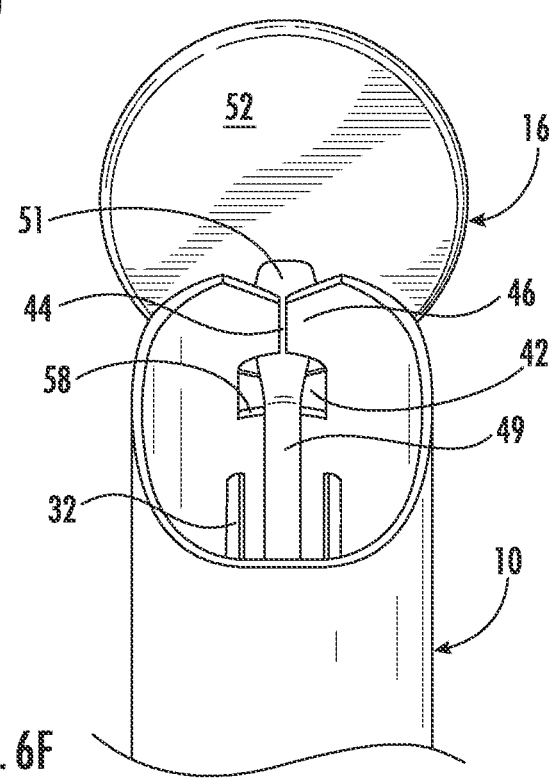
Figure 7:
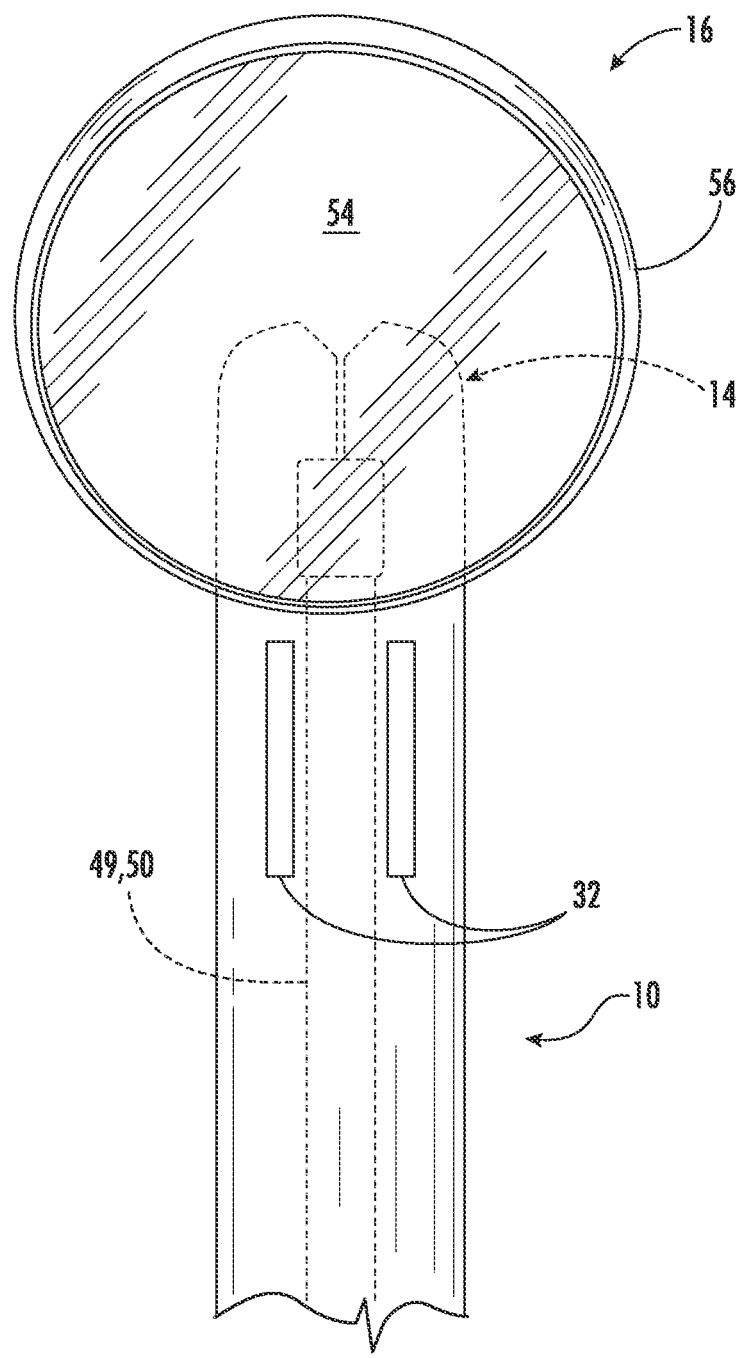
FIG. 7 is a front pictorial view of the combination of FIG. 6B.
Figure 8:
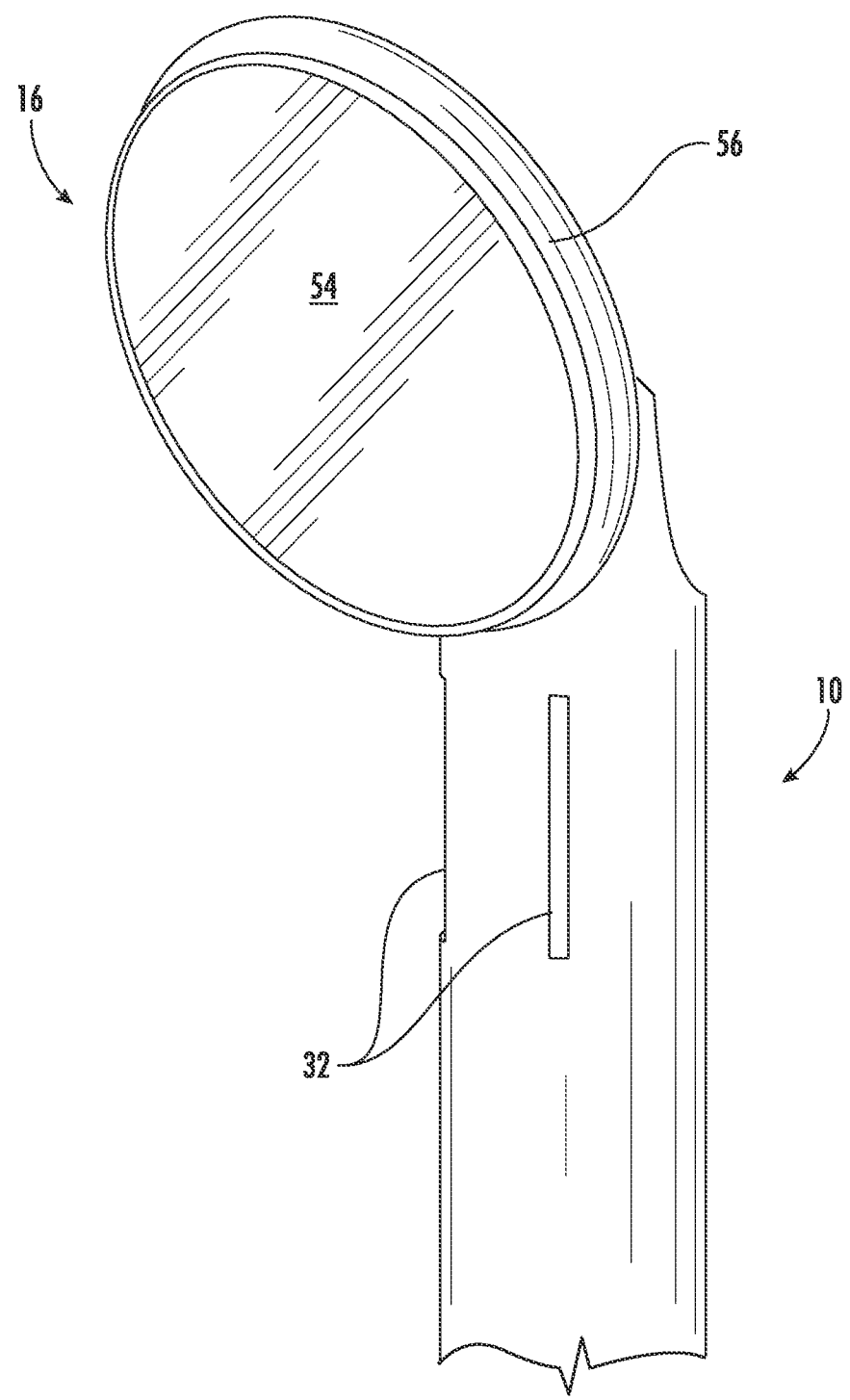
FIG. 8 is a right-front pictorial view of the combination of FIG. 6B.
Figure 9:
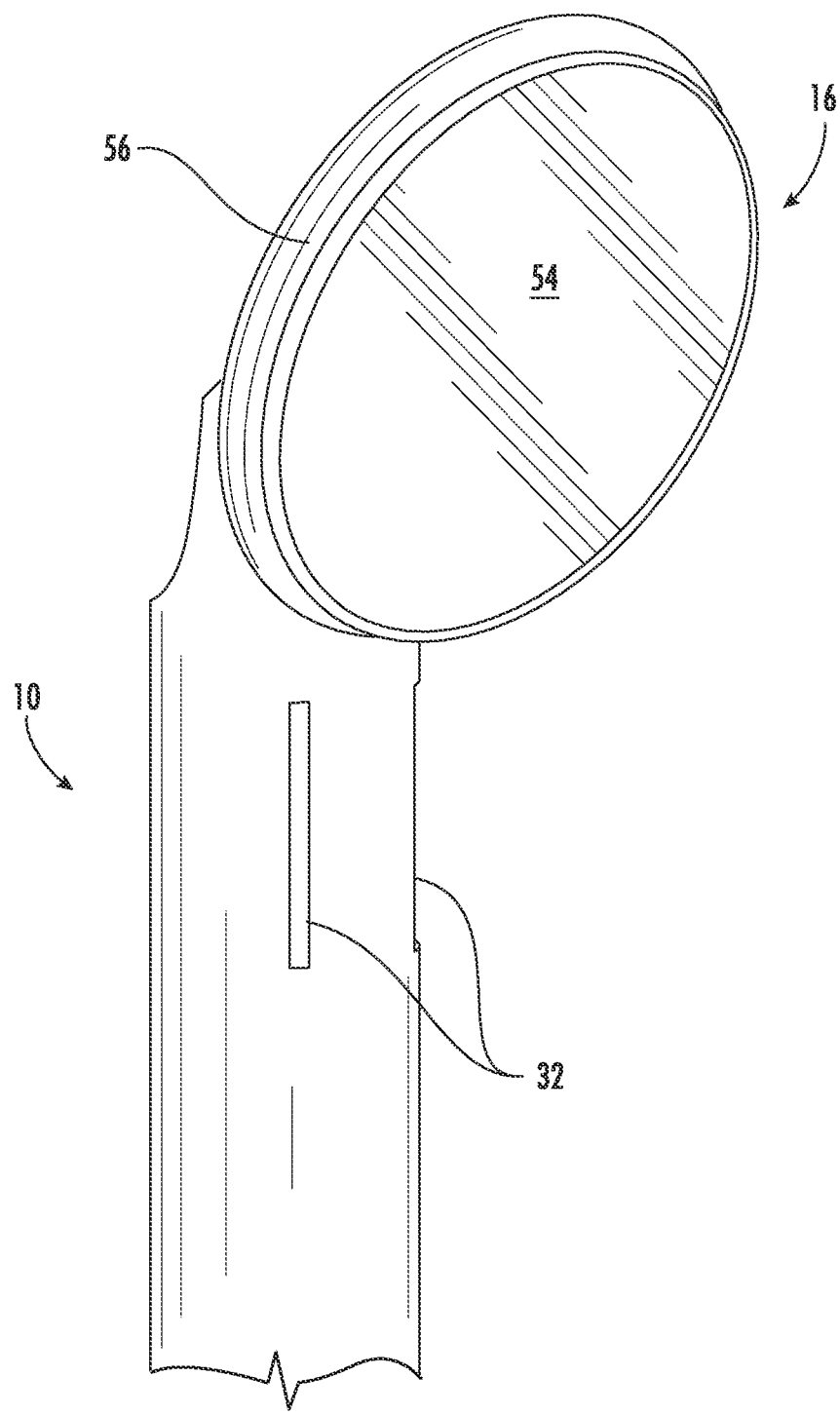
FIG. 9 is a left-front pictorial view of the combination of FIG. 6B.

In the first and second embodiments, and as best understood with reference to FIGS. 6D and 6E, the relative movement between the tube 10 and at least the stem 49 typically results in the rod, stem 49 and/or mounting tab 51 engaging the beveled edges 72 so that the rod, stem 49 and/or mounting tab 51 is guided into the guideway slot 44. As the relative movement continues, the rod, stem 49 and/or mounting tab 51 passes from the upper end of the guideway slot 44, through the guideway slot 44, and into the receptacle or mounting hole 42. When the rod, stem 49 and/or mounting tab 51 extends through the receptacle or mounting hole 42, the mounting or engagement tabs 46 typically engage a back side of the mirror apparatus 16 (e.g., bezel 56, neck, stem 49, mounting tab 51, and/or the like), as discussed further below.

Referring to FIG. 6E, the first and second embodiment tubes 10, or at least the engagement tabs 46, are typically constructed of a sufficiently elastic material (e.g., polymeric material) so that the engagement tabs 46 pivot and/or deform to widen the guideway 44 and allow the stem 49, neck, mounting tab 51, and/or the like to be forced through the guideway 44. That is, the stem 49, neck, mounting tab 51, and/or the like is typically more rigid than the engagement tabs 46 so that the engagement tabs temporarily bend (e.g., are deflected) in response to the respective portion of the mirror apparatus 16 being forced through the guideway 44, to temporarily widen the guideway 44. After the stem 49, neck, mounting tab 51, and/or the like is forced through the guideway 44, the engagement tabs 46 typically seek to elastically return toward their original configuration to narrow or at least partially close the guideway 44, and the engagement tabs may at least partially hold the mirror apparatus 16 in place for example by at least partially providing a snap-fit connection, or the like, as discussed further below.

As an example, when the mirror apparatus 16 is fully mounted to the tube 10, the engagement tabs 46 can optionally be slightly deflected inwardly so that they are firmly engaged against, and apply force against, the rear side of the mirror apparatus' head (e.g., neck, stem 49, mounting tab 51, and/or the like) in a manner so that the mirror apparatus 16 is fixedly (e.g., yet removably) mounted to the tube 10, for example by at least partially providing a snug snap-fit connection, or the like, as discussed further below. Additionally, for the first and second embodiments, at least a portion of the mirror apparatus 16 (e.g., the handle 50 and/or stem 49) can be firmly engaged against at least one interior surface of the tube 10 for helping to fixedly secure the mirror apparatus 16 to the tube 10, as discussed further below.

At least partially reiterating from above and in accordance with the first and second embodiments, the tubular body 10 and the mirror apparatus 16 can be cooperatively configured to provide a snap-fit connection between the mirror apparatus 16 and the dental evacuation tip 10. In this regard, the tab portions 46 of the tubular body 10 can be snap-fit connector parts of the snap-fit connection between the mirror apparatus 16 and the dental evacuation tip 10. In this regard and referring to FIGS. 6B-6F, a method can include causing relative movement between the dental evacuation tip 10 and the mirror apparatus 16 so that at least a portion of the rod 49 and/or 50 of the mirror apparatus is positioned in the interior passageway, and fastening the mirror apparatus to the dental evacuation tip while at least the portion of the rod is positioned in the interior passageway, wherein the fastening can include providing the snap-fit connection between the mirror apparatus to the dental evacuation tip.

The engagement tabs or snap-fit connector parts 46 can be flexibly configured to be deformed to at least temporarily enlarge the guideway slot 44 for allowing the rod, stem 49 and/or mounting tab 51 to be passed through the guideway 44 and be received in the receptacle 42. The engagement tabs or snap-fit connector parts 46 can be elastically configured to engage a backside of the mirror apparatus 16 (e.g., the stem 49, mounting tab 51, and/or the like) to releasably secure, or at least partially releasably secure, the mirror apparatus to the tubular body 10.

In the first and second embodiments, the tubular body 10 and mirror apparatus 16 are cooperatively configured so that the tubular body's edge 58 (FIGS. 5A, 6B, and 6D-6F) that partially defines the receptacle 42, or an adjacent portion of the tubular body 10, functions as a fulcrum that engages the rod, stem 49, and/or mounting tab 51. In the first and second embodiments, the elastic tabs or snap-fit connector parts 46 may be deformed inwardly due to their engagement with the back side of the mirror apparatus 16 (e.g., against the back side of the mirror apparatus' stem 49 and/or mounting tab 51), and the tab parts 46 seeking to return to their at-rest configuration may apply force against the back side of the mirror apparatus 16 (e.g., against the back side of the mirror apparatus' mounting tab 51 or distal portion of the stem 49). As a result, the rod 49 and/or 50 engages and pivots about the fulcrum (e.g., the tubular body's edge 58, or the like) so that the proximal end portion of the rod or handle 50 engages the inside surface of the tubular body 10 (see, e.g., FIGS. 6C and 10).

Referring to FIG. 6C, in the first and second embodiments, the proximal end portion of the rod or handle 50 can engage the inside surface of the tubular body 10 that is opposite from the fulcrum (e.g., opposite from the tubular body's edge 58) so that at least a portion of the mirror apparatus' handle 50, stem 49, extension, body part, and/or rod is fixedly (yet removably) lodged in the tube's interior passageway. As a result, in an example of using the system of the first and second embodiments, the mirror apparatus' handle 50, stem 49, extension, body part, and/or rod extends obliquely relative to the lengthwise axis of the tube 10

FIG. 10 depicts the tube 10 of FIGS. 1-5B mounted to both the mirror apparatus 16 and fitting 13, as discussed above. In FIG. 10, the entire shaft or handle 50 of the mirror apparatus 16 is schematically depicted with dashed lines as being hidden from view within the tube 10. Referring to FIGS. 6C and 10, the mirror apparatus' handle 50, stem 49, extension, body part, and/or rod can extend obliquely relative to the lengthwise axis of the tube 10, so that the proximal end portion of the handle and/or stem engages against an inner surface of the tube in a manner that braces and stabilizes the mirror apparatus 16 and, thus, restricts relative movement between the mirror apparatus and the tube. In this regard, the mirror apparatus' handle 50, stem 49, extension, body part, and/or rod can engage against the inner surface of the tube 10 that is opposite from the proximal intake hole 34 so that the mirror apparatus' rod, handle and/or stem neither obstructs the proximal intake hole nor substantially restricts flow through the proximal intake hole. Similarly and as best understood with reference to FIGS. 6B and 6F, the distal openings or slots 32 can be laterally spaced apart from the mirror apparatus' handle 50, stem 49, extension, body part, and/or rod (e.g., respectively positioned apart from opposite sides of the rod) so that the mirror apparatus' rod, handle and/or stem neither obstructs the distal intake holes nor substantially restricts flow through the distal intake holes.

In the first and second embodiments, and as best understood with reference to FIGS. 6B, 6C, and 10, the engagement tabs 46 engage the back side of the mounting tab 51 or the distal end portion of the rod or stem 49 (e.g., first engagement area(s)), the tube's fulcrum or edge 58 engages an intermediate portion of the rod or stem 49 (e.g., second engagement area), and the inside surface of the tube 10 engages the proximal end portion of the rod or handle 50 (third engagement area). The first through third engagement areas can be spaced apart along the length of the tube 10 and respectively positioned on opposite sides of the tube so that at least a portion of the mirror apparatus' handle 50, stem 49, extension, body part, and/or rod is fixedly (yet removably) lodged in the tube's interior passageway. With continued reference to FIGS. 6B and 6C, the second and third engagement areas of the first and second embodiments are not annular, and along the length of the tube 10 an elongate, annular gap that is defined between the inner surface of the tube 10 and outer surface of the mirror apparatus' handle 50, stem 49, extension, body part, and/or rod extends between the second and third engagement areas. The elongate annular gap can extend along the length of the tube from the second engagement area to the third engagement area. In the first and second embodiments, the mirror apparatus' handle 50, stem 49, extension, body part, and/or rod within the interior space of the tube 10 only partially obstructs the tube's interior passageway so that there can be suction-induced flow through the entire length of the tube's interior passageway. Stated differently, the mirror apparatus' handle 50, stem 49, extension, body part, and/or rod within the interior space of the tube 10 only partially obstructs the suction-induced flow through the interior pathway of the tube. Alternatively, the elongate annular gap may extend for a shorter length, there may be differently configured engagement areas, and other variations are within the scope of this disclosure. The mirror apparatus 16 can be removed from the tube 10 by substantially reversing the above-described process, or the like.

FIG. 10 further schematically depicts the mounted-together tube 10 and mirror apparatus 16 being used in a patient's open mouth. The mouth includes a tongue 60 and teeth 62. FIG. 10 further schematically depicts other parts of the patient, for example the patient's sinus cavity 64. In an example of a method of using the tube 10 in the configuration depicted in FIG. 10, suction (e.g., a partial vacuum) is supplied to the interior of the tube's proximal end 14 by way of the fitting 13 and/or other suitable features.

In the example depicted in FIG. 10, the distal intake slots 32 are positioned in the patient's mouth so that aerosols from within the patient's mouth can be drawn into the distal intake slots. The one or more slots 32 can be sufficiently adjacent to the mirror 54 so that at least some of the aerosols and/or air drawn into the slots travels across the surface of the mirror 54 in a manner that seeks to prevent condensation on the mirror and/or seeks to pull droplets off of the mirror (e.g., dry the mirror), or the like.

In contrast to the distal intake slots 32, the proximal intake slots 30 are positioned outside of, yet proximate or adjacent to, the patient's mouth for intaking at least any aerosol that may have exited the patient's mouth. The size and configuration of the tube 10 (e.g., the sizes and positions of the features of the tube) can be adjusted or tuned for being accommodated to different uses, for example for being used in differently sized mouths, for being used during different dental procedures, and/or the like. For example, the tube 10 can be shorter than depicted in FIG. 10 and/or the handle portion 50 of the mirror apparatus 16 can be omitted from the combination depicted in FIG. 10.

With continued reference to FIG. 10, a user can selectively use one or more of their fingers to at least partially block at least a portion of one or more of the proximal intake slots 30, or the like, to adjust the amount of suction supplied to the distal intake slots 32 and the tube's distal end opening 15 (see, e.g., FIGS. 1 and 6). Similarly, in an example of a method of using the tube 10 depicted in FIG. 5C, a user can selectively use one or more of their fingers to at least partially block at least a portion of the at least one proximal intake hole 34 to adjust the amount of suction supplied to the distal intake slots 32 and the tube's distal end opening 15.

After use of the connected-together tube 10 and mirror apparatus 16, the tube and mirror apparatus can be disconnected from one another by reversing the above-discussed mounting process. Typically the tube 10 is a disposable item that is separated from the fitting 13 and mirror apparatus 16 after being used with a patient, so that the tube can be discarded, and the fitting and mirror apparatus may be sterilized and reused.

At least partially reiterating from above, the tube 10 is typically constructed of a disposable material (e.g., polymeric material) that is both sufficiently rigid for maintaining the overall tubular shape of the tube, and sufficiently elastic so that the engagement tabs 46 pivot and/or deform to widen the guideway 44 and allow the stem 49, neck, mounting tab 51, and/or the like to be forced through the guideway 44. If necessary or helpful, for example for more securely gripping or retaining the mirror apparatus 16, at least the engagement tabs 46 can be strengthened or rigidified in any suitable manner, for example by the engagement tabs 46, or more generally the distal end portion of the tube, having a greater thickness than the remainder of the tube 10.

Figure 11:
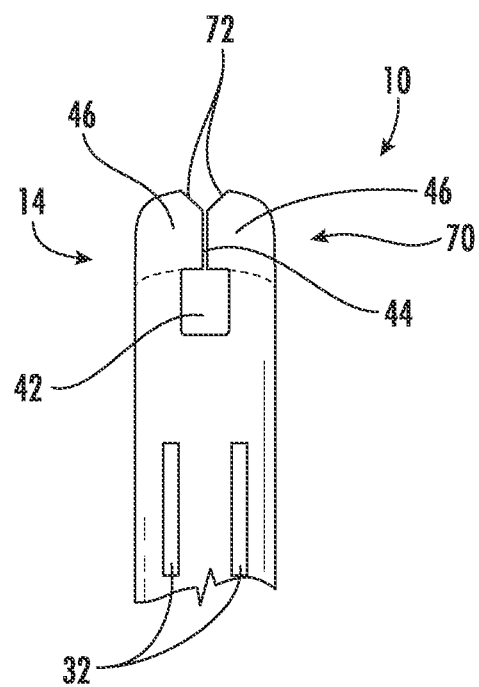
FIG. 11 is a front elevation view of an upper portion of an evacuation tip in accordance with a third embodiment of this disclosure.
Figure 12:
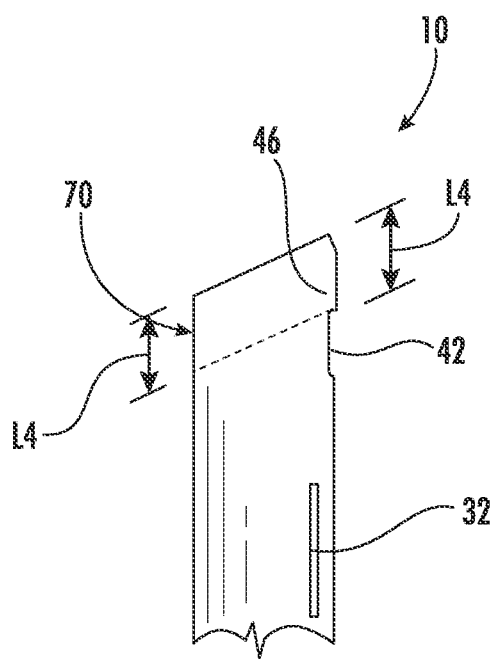
FIG. 12 is a left elevation view of the portion of the evacuation tip of FIG. 11, wherein a right elevation view of the portion of the evacuation tip of FIG. 11 is a mirror image of FIG. 12.

Other embodiments are within the scope of this disclosure. For example, FIGS. 11 and 12 depict a distal end portion 14 of a tube 10 in accordance with a third embodiment of this disclosure. The first through third embodiments can be alike, except for variations noted and variations that will be apparent to those of ordinary skill in the art.

Referring to FIGS. 11 and 12, a generally annular end portion 70 (a boundary of which is schematically depicted with dashed lines) includes the engagement tabs 46 and can have a different or greater thickness than the reminder of the tubular body 10, for strengthening or rigidifying the engagement tabs. The end portion 70 may extend along the length of the tube for a length L4 (FIG. 12) of about 4 millimeters. The end portion 70 may have a wall thickness that exceeds the wall thickness of the remainder of the tube by about 0.25 millimeters. For easing of the insertion of the stem 49, neck, mounting tab 51, and/or the like (FIGS. 6A and 6B) through the mounting opening or guideway 44, the outer end of the mounting opening or guideway 44 can be tapered. The taper can be defined by one or more beveled edges 72 (FIG. 11) that may each extend for about 1 millimeter. The values recited in this paragraph can vary, for example, by plus or minus 5 percent, plus or minus 10 percent, plus or minus 15 percent, plus or minus 20 percent, plus or minus 25 percent, plus or minus 50 percent, or any subranges or values therebetween.

Other embodiments are within the scope of this disclosure. For example, FIGS. 13-16 depict a tubular body 10 in accordance with a fourth embodiment of this disclosure. The first through fourth embodiments can be alike, except for variations noted and variations that will be apparent to those of ordinary skill in the art.

Referring to FIGS. 13-16, the mounting feature or hole 42 may be referred to as a distal mount, distal mounting hole, or distal receptacle since it is proximate or adjacent the tube's distal end 14. Also, the distal mount of the fourth embodiment can optionally omit the relatively narrow slit or slot-like guideway 44 of the first and second embodiments so that the distal mounting hole or receptacle 42 extends to and/or is at least partially defined by the tube's distal end 14.

Figure 13:
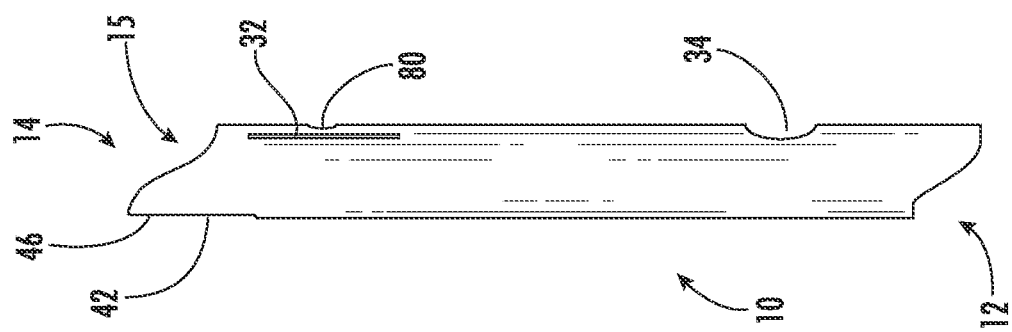
FIGS. 13-16 respectively are front, rear, right, and left elevation views of an evacuation tip in accordance with a fourth embodiment of this disclosure.
Figure 14:
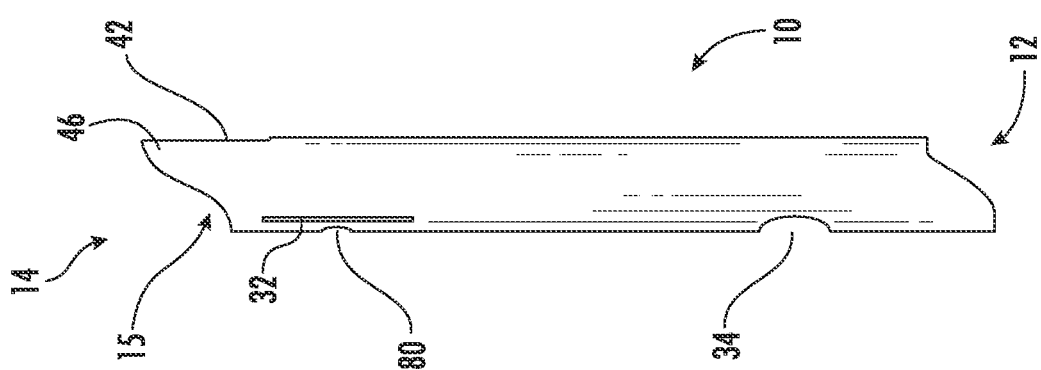
Figure 15:
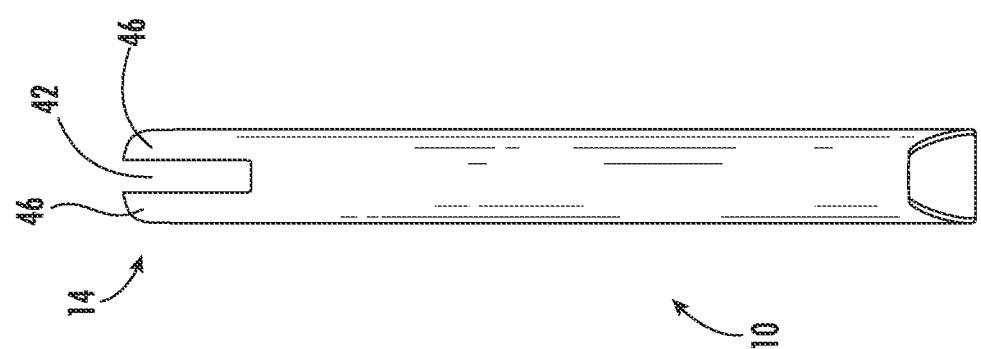
Figure 16:
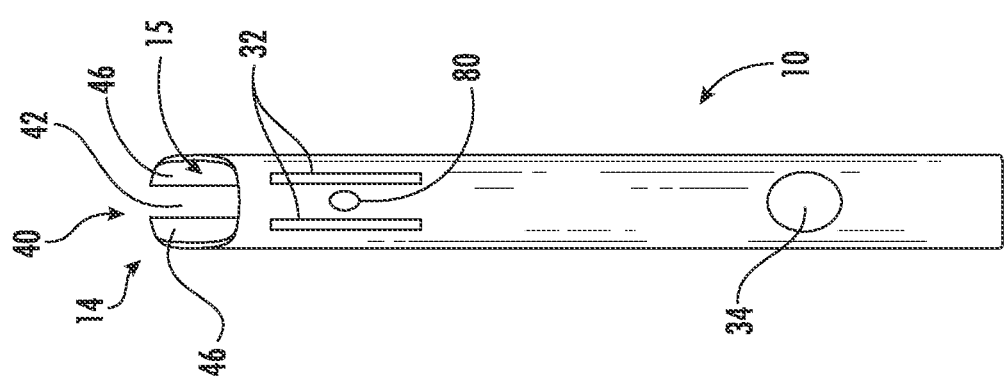

Referring to FIGS. 13, 15, and 16, the at least one mount can further include a proximal hole or receptacle 80 that extends through the sidewall of the tube 10. The proximal mounting receptacle or hole 80 can be positioned on the opposite side of the tube 10 from the distal mounting receptacle or hole 42. The proximal mounting hole or receptacle 80 can be positioned between the distal intake slots 32 or in any other suitable location. The distal and proximal mounts or mounting receptacles 42, 80 can be spaced apart from one another along the length of the tube 10, and can be positioned diagonally apart from one another across the tube's interior passageway.

An example of a method of removably mounting at least a portion of the mirror apparatus 16 to the tube 10 of the fourth embodiment can be best understood by referring to FIGS. 6A and 13-20. As best understood with reference to FIG. 6A, the handle 50, if present, can be removed from the remainder of the mirror apparatus 16 by, for example, causing relative rotation between the handle and the stem 49 so that an externally screw-threaded proximal end portion of the stem becomes separated from an internally screw-threaded distal end of the handle.

With the mirror apparatus' handle 50 separated from the reminder of the mirror apparatus 16, initially the proximal end of the mirror apparatus' stem 49 (e.g., an extension, rod, shaft, and/or other suitable structure connected to the mirror apparatus' head) can be inserted through the tube's distal end opening 15 and into the tube's interior space. Then, the stem 49 can be guided farther through the distal end opening 15 and obliquely farther into the tube's interior space so that the proximal end of the stem 49 travels in the tube interior space toward the tube's proximal end 12, or more specifically toward the tube's proximal mounting hole or receptacle 80.

Referring to FIGS. 17-20, the oblique relative movement between the tube 10 and mirror apparatus 16 (e.g., without the handle 50) typically continues until the stem's proximal end extends through the proximal mounting hole or receptacle 80, a central portion of the stem 49 extends through the distal mounting hole or receptacle 42 and optionally engages against at least an edge of the tube 10 that defines a proximal end of the distal mounting hole or receptacle 42, and the rear sides of the engagement tabs 46 engage the mirror 54.

Figure 19:
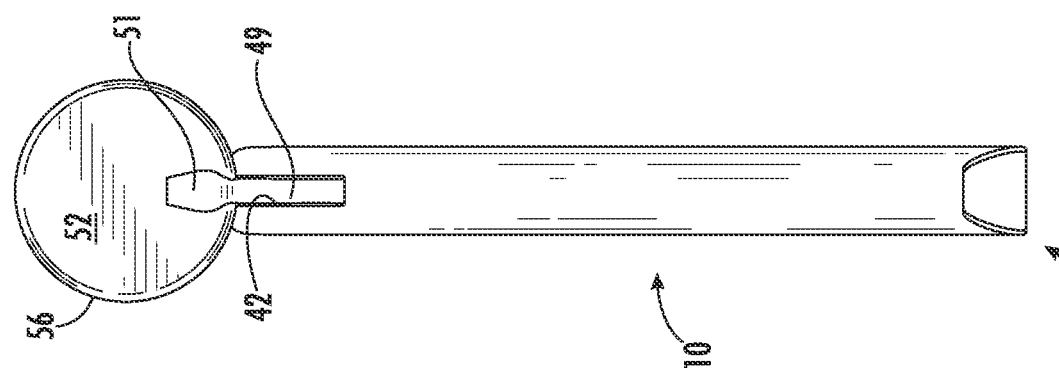
Figure 20:
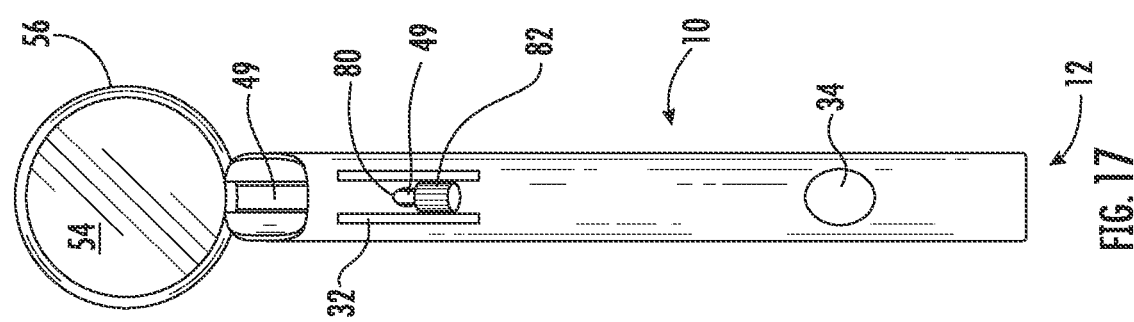
FIG. 20 is a partially exploded, left elevation view of the combination of FIGS. 17-19, in accordance with an embodiment of this disclosure.

In FIGS. 19 and 20, the central portion of the stem 49 is schematically depicted with dashed lines as being hidden from view within the tube 10. The stem 49 can extend obliquely relative to the lengthwise axis of the tube 10, so that the stem engages against respective portions of the tube in a manner that braces and stabilizes the mirror apparatus 16 (e.g., without the handle 50) and, thus, restricts relative movement between the mirror apparatus and the tube.

In the fourth embodiment, the mirror apparatus 16 (e.g., without the handle 50) is both fixedly and removably connected to the tube 10 when the stem's proximal end extends through the proximal receptacle 80, a central portion of the stem 49 extends through the distal receptacle 42 and optionally engages against at least an edge of the tube that defines a proximal end of the distal receptacle 42, and the rear sides of the engagement tabs 46 engage the mirror 54. This connection can be provided by an interference fit between the stem's proximal end and one or more surfaces of the tube 10 that define (e.g., an annular edge of the tube that defines) the proximal receptacle 80, an interference fit between the central portion of the stem 49 and respective (e.g., opposite) surfaces of the tube 10 that at least partially define the distal receptacle 42, and/or at least one fastening feature or fastener 82 attached to the portion of the stem's proximal end 12 that extends outwardly from the proximal receptacle 80 or is in any other suitable configuration.

The fastening feature or fastener 82 can be, for example, a clip, or a nut having internal screw thread(s) configured to mesh with external screw thread(s) of the proximal end portion of the stem 49, and/or any other suitable fastening feature. In the fourth embodiment, the fastener or fastener part is a nut 82 that can be, for example, a conventional square or hexagonal nut, a conventional coupling nut, a conventional wing nut, a nut with a knurled outer surface, and/or or any other suitable nut, or the like. The outer overall dimensions of the nut 12 can be larger than the diameter or cross-wise dimension of the proximal receptacle 80. As a result, the internally screw-threaded nut 12 can be screwed onto the externally screw-threaded proximal end portion of the stem 49 that extends outwardly from the proximal receptacle 80 to releasably secure the mirror apparatus 16 (e.g., without the handle 50) to the tube 10.

Figure 17:
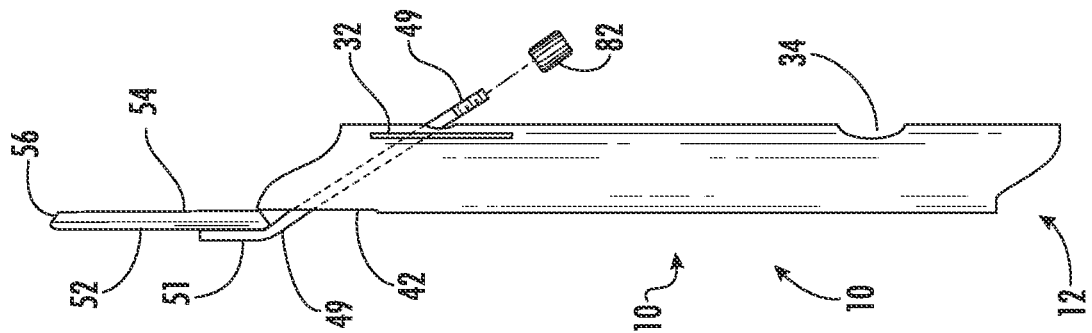
FIGS. 17-19 respectively are front, rear, and right elevation views of a mirror apparatus mounted to the evacuation tip of FIGS. 13-16, in accordance with an embodiment of this disclosure.
Figure 18:
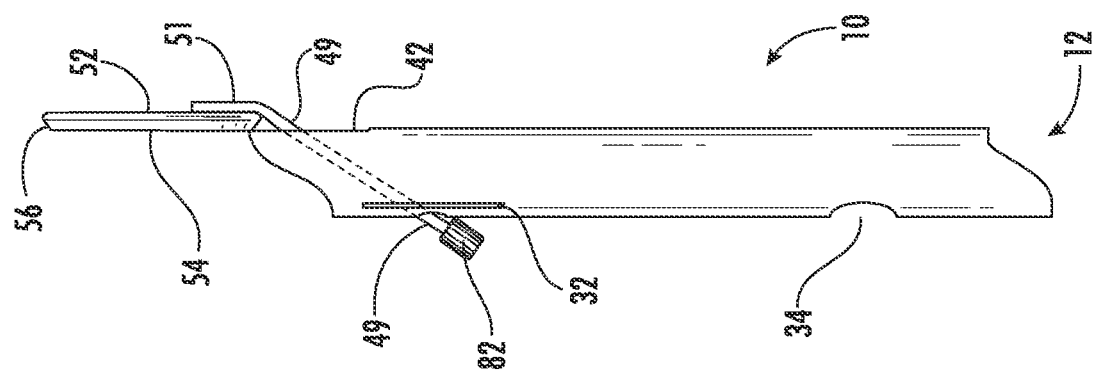

In FIGS. 17 and 19, the nut 12 is depicted as being mated to the threaded proximal end portion of the stem 49 to releasably secure the mirror apparatus 16 to the tube 10. In FIG. 20, the nut 82 is depicted as being exploded away from the threaded proximal end portion of the stem 49 so that the mirror apparatus 16 can be removed from the tube 10.

In the fourth embodiment, the mirror apparatus 16 can be fixedly (yet still removably) attached to the tubular body 10 by way of the fastener part or nut 82 being connected to (e.g., threadedly screwed onto) the rod or stem 49 with sufficient force so that the fastener part or nut forcibly engages against the front outer surface of the tube (e.g., first engagement area), the head (e.g., bezel 56 and/or mirror 54) of the mirror apparatus 16 forcibly engages against the rear outer surface of the tube (second engagement area(s)), a majority of the length of the rod or stem 49 is in tension, and the portion of the tube between the first and second engagements areas is in compression. The nut 82 or other suitable fastening parts or components can be made of metallic material, polymeric material, and/or other suitable materials. Additional and/or different fastening mechanisms can be used to releasably secure the mirror apparatus 16 to the tube 10.

In the fourth embodiment, the maximum outer diameter of the stem 49 is typically smaller than the inner diameter D1 (FIG. 4) of the tube 10, so that the stem does not prevent fluid from flowing through the interior space of the tube 10. Stated differently, the mirror apparatus' extension or body part (e.g., the rod or stem 49) within the interior space of the tube 10 only partially obstructs the interior passageway of the tubular body 10 (e.g., the suction-induced flow through the interior flowpath of the tube). Accordingly, the mirror apparatus' handle 50, stem 49, extension, body part, and/or rod within the interior space of the tube 10 only partially obstructs the tube's interior passageway so that there can be suction-induced flow through the entire length of the tube's interior passageway.

After use of the connected-together tube 10 and mirror apparatus 16 (e.g., without the handle 50), the tube and mirror apparatus can be disconnected from one another by reversing the above-discussed mounting process. Typically the tube 10 is a disposable item that is separated from the fitting 13 and mirror apparatus 16 after being used with a patient, so that the tube can be discarded, and the fitting and mirror apparatus may be sterilized and reused.

In the fourth embodiment and a fifth embodiment, the handle 50 (FIG. 6A) is typically omitted from the mirror apparatus, and the mirror apparatus can be characterized as further including, or being associated with, the at least one fastener 82 (e.g., nut) and/or other suitable fastening features. The first through fifth embodiments can be alike, except for variations noted and variations that will be apparent to those of ordinary skill in the art.

FIGS. 21-25 depict a tubular body 10 in accordance with the fifth embodiment. As schematically depicted with dashed lines in FIG. 21, optionally one or more of the above-discussed intake holes 30, 32, or the like, can extend through the sidewall of the tube 10. Reiterating from above, the tube 10 may have any suitable length extending between its opposite proximal and distal ends 12, 14.

Referring to FIGS. 21-24, the tube's mounting opening or hole 42 may be referred to as a distal mount, distal mounting hole, or distal receptacle since it is proximate or adjacent the tube's distal end 14. In the fifth embodiment, the distal mounting feature or hole 42 is defined by (at least partially defined by) at least one edge 90 (e.g., a curved or arcuate edge) of the tube 10. In the fifth embodiment, the edge 90 is proximate, extends to, and/or at least partially defines the tube's distal end 14 and distal end opening 15, so that the distal mounting feature, opening, or hole 42 may extend to, or be at least partially defined by, the tube's distal end. The distal mounting feature, space, opening, or hole 42 can be a respective portion of the tube's distal end opening 15, or the like. For example, the at least one edge 90 that defines the distal mounting feature, space, opening, or hole 42 may be referred to as the tube's distal end edge(s) 90.

Referring to FIGS. 22-25, the fifth embodiment tube 10 further includes a proximal mounting space, opening, or hole 80 that extends through and/or is at least partially defined by the sidewall of the tube 10. The proximal receptacle 80 can be positioned on the same side (e.g., the rear side) of the tube 10 as the distal mounting feature or hole 42. The distal and proximal mounting holes or receptacles 42, 80 can be spaced apart from one another along the length of the tube 10.

Figure 25:
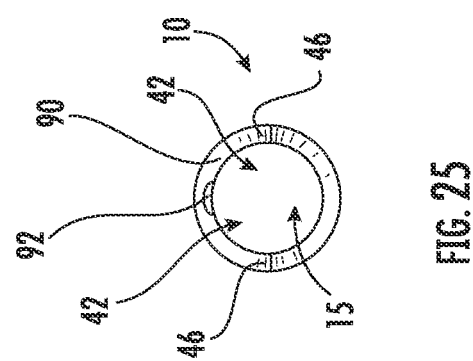
FIG. 25 is a top plan view of the evacuation tip of the fifth embodiment.

Referring to FIGS. 21, 22 and 25, there can be one or more structural features inside of the tube 10 and/or defined by the inner surface of the tube, wherein these feature(s) can be configured to guide, align, and/or otherwise assist with the mounting of the mirror assembly. For example, an elongate mounting receptacle, recess, or channel 92 can be defined by the inner surface of the tube 10. The guiding or mounting channel 92 can extend, for example, from one to the other of the mounting holes or receptacles 42, 80 along the length of the tube 10.

An example of a method of removably mounting a mirror apparatus to the fifth embodiment tube 10 is described in the following, in accordance with an embodiment of this disclosure. As best understood with reference to FIG. 6A, the handle 50, if present, can be removed from the remainder of the mirror apparatus 16 by, for example, causing relative rotation between the handle and the stem 49 so that the externally screw-threaded proximal end portion of the stem becomes separated from the internally screw-threaded distal end of the handle.

Figure 28:
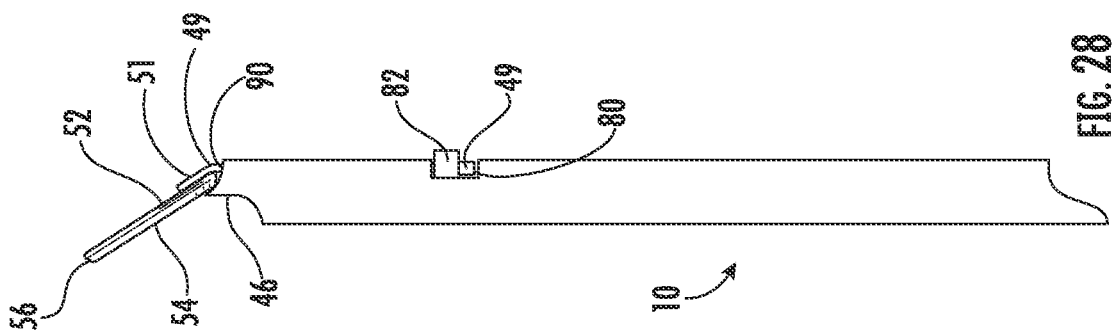
FIGS. 26-28 respectively are front, rear, and right elevation views of a mirror apparatus mounted to the evacuation tip of FIGS. 21-25, wherein a left elevation view of the combination of FIGS. 26-28 can be a mirror image of FIG. 28, in accordance with an embodiment of this disclosure.
Figure 29:
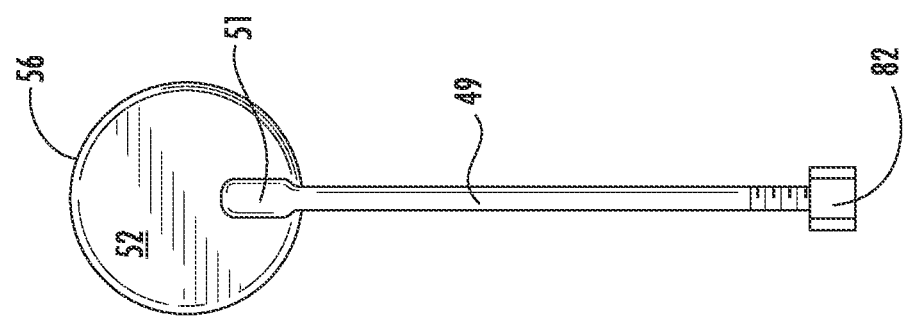
FIG. 29 is a rear elevation view of the mirror apparatus with a nut in a proximal position, in accordance with an embodiment of this disclosure.

Referring to FIG. 29, at least one fastener 82 or other suitable fastening feature can be manually attached to the stem's proximal end portion. The fastener 82 can be, for example, a clip, or a nut having internal screw thread(s) configured to mesh with external screw thread(s) of the proximal end portion of the stem 49, and/or any other suitable fastening feature. In the embodiment depicted in FIGS. 30 and 31, the outer overall dimensions of the nut 12 are smaller than the corresponding cross-wise dimensions of the proximal mounting hole or receptacle 80 (FIGS. 22-24, 27, 28, 30, and 31), as discussed further below.

Figure 30:
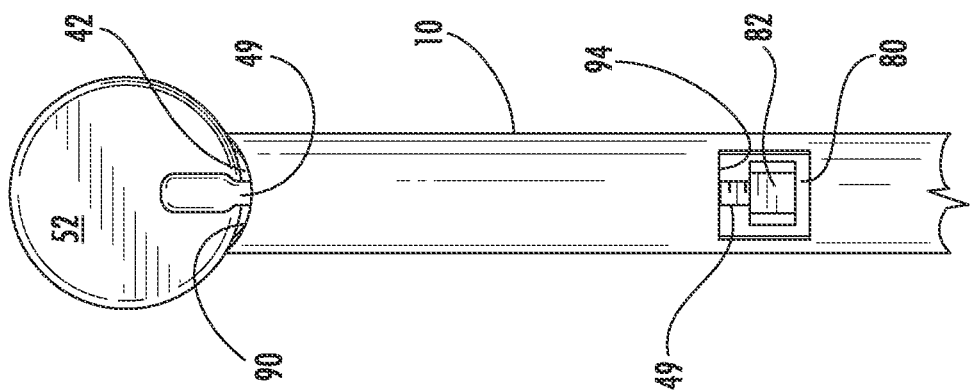

FIGS. 29 and 30 can be characterized as depicting the fastener part or nut 82 in a proximal position along the length of the stem 49. In contrast, FIGS. 27, 28, and 31 can be characterized as depicting the nut 82 in a distal position along the length of the stem 49. The nut 82 can be transitioned between the proximal and distal positions along the length of the stem 49 by way of manually implemented relative rotation between the nut and stem, and the associated interaction between the screw threads of the nut and stem.

With the fastener part or nut 82 in its proximal position as shown in FIG. 29, initially the proximal end of the mirror apparatus' stem 49, with the nut 82 connected thereto, can be manually inserted through the tube's distal end opening 15 and/or the distal receptacle 42 and into the tube's interior space. Then, the stem 49 carrying the nut 82 can be manually guided farther through the distal end opening 15 and/or the distal receptacle 42 into the tube's interior space so that the proximal end of the stem 49, with the nut 82 thereon, travels in the tube interior space toward the tube's proximal end 12, or more specifically toward the tube's proximal receptacle 80.

Figure 26:
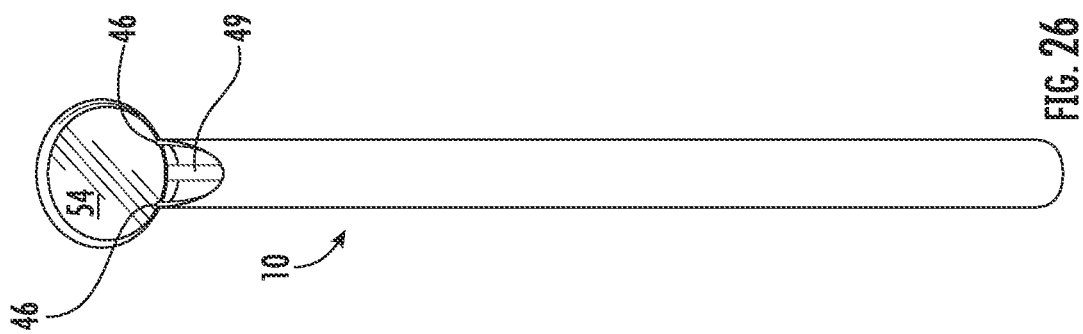

Referring to FIGS. 26, 28, and 30, the manually implemented relative movement between the tube 10 and mirror apparatus typically includes both lengthwise and lateral relative movement. The lengthwise relative movement typically includes causing the fastener part or nut 82 on the stem's proximal end to become adjacent the proximal receptacle 80. The lateral relative movement typically includes causing a portion of the nut 82 on the stem's proximal end to extend outwardly through the proximal receptacle 80.

The relative movement typically continues until the distal end portion of the stem 49 extends through the distal receptacle 42, the rear sides of the engagement tabs 46 engage the mirror 54, the predetermined portion of the nut 82 on the stem's proximal end extends outwardly through the proximal receptacle 80, a central portion of the stem 49 engages the rear interior surface of the tube 10, and optionally the rearward portion of the central portion of the stem 49 fits into the channel 92 (FIGS. 21 and 22).

Then, the mounting can be completed by manually transitioning the nut 82 from the proximal position (FIGS. 29 and 30) to the distal position (FIGS. 27, 28, and 30) so that an end of the nut firmly engages at least one predetermined edge 94 of the tube 10 that at least partially defines the proximal receptacle 80. In the fifth embodiment, the tube's edge 94 is positioned between the tube's opposite ends 12, 14. For example, the at least one edge 94 may be referred to as the tube's intermediate edge(s) 94.

The transitioning of the nut 82 from the proximal position (FIGS. 29 and 30) to the distal position (FIGS. 27, 28, and 30) so that, for example, the upper end of the nut firmly engages the tube's intermediate edge 94 can be facilitated by a user manually engaging the portion of the nut 82 that extends outwardly through the proximal receptacle 80 in a manner that causes the nut to rotate relative to the stem 49 and travel along the stem toward the head/mirror 54 of the mirror apparatus by way of the associated interaction between the screw threads of the nut and stem.

Figure 27:
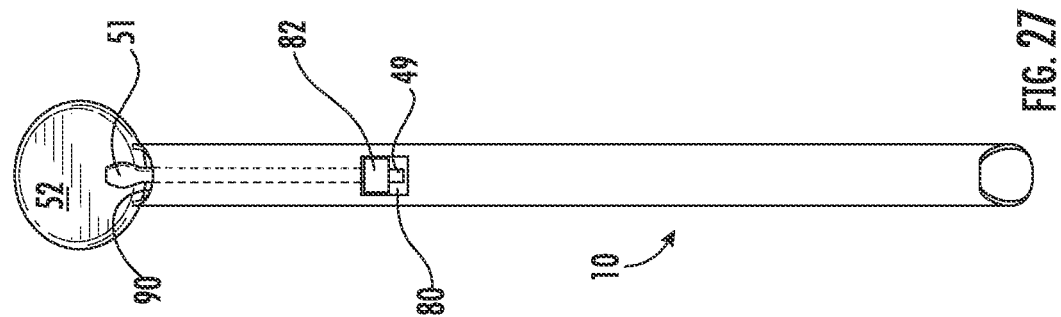
Figure 31:
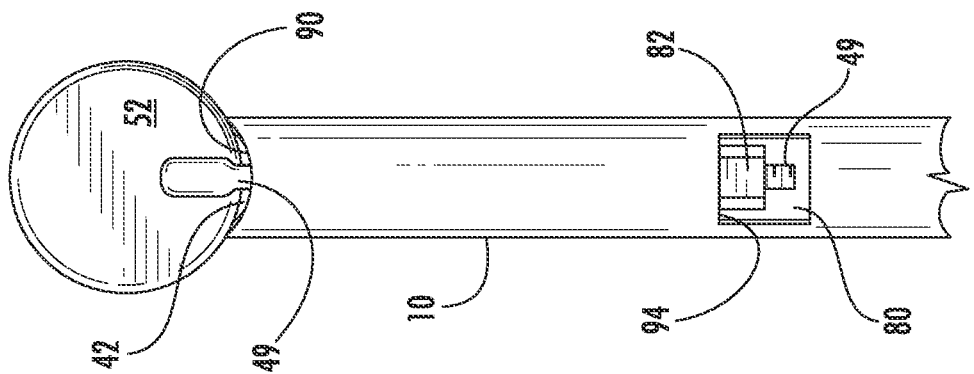
FIGS. 30 and 31 depict configurations/aspects of a method of mounting the mirror apparatus to a portion of the evacuation tip of FIGS. 21-25, wherein the nut is in the proximal position in FIG. 30, and the nut is in a distal position in FIG. 31, in accordance with an embodiment of this disclosure.

FIGS. 27, 28, and 31 depict the mirror apparatus mounted to the tube 10 so that the nut 82 is in the distal position along the length of the stem 49, the predetermined end of the nut firmly engages the tube's intermediate edge 94 that at least partially defines the proximal receptacle 80, the mirror apparatus' head firmly engages the tube's distal end edge 90 that at least partially defines the distal mounting feature or hole 42, the distal end portion of the stem 49 extends through the distal receptacle 42, the rear sides of the engagement tabs 46 engage the mirror 54, a predetermined portion of the nut 82 extends outwardly through the proximal receptacle 80, the central portion of the stem 49 engages the rear interior surface of the tube 10, and optionally the rearward portion of the central portion of the stem 49 fits into the channel 92 (FIGS. 21 and 22).

Responsive to the predetermined end of the nut 82 firmly engaging the tube's intermediate edge 94 (and/or other suitable structure) and the mirror apparatus' head firmly engaging the tube's distal end edge 90 (and/or other suitable structure), a predetermined portion of the stem 49 is in tension and a predetermined portion of the tube 10 is in compression in a manner so that the mirror apparatus is fixedly connected to the tube 10. The mirror apparatus can be removed from the tube 10 by reversing the process of mounting the mirror apparatus to the tube.

At least partially reiterating from above, the outer overall dimensions of the nut 12 can be about the same size as, or at least slightly smaller than, the corresponding cross-wise dimensions of the proximal receptacle 80 (FIGS. 22-24, 27, 28, 30, and 31) so that the nut can be rotated while protruding outwardly through the proximal receptacle as part of the above-described mounting process. When the nut 12 and/or other suitable fastener(s) protrude outwardly through the proximal receptacle 80, the nut 12 and/or other suitable fastener(s) at least partially obstruct the proximal receptacle 80. The relative positions and/or dimensions of the fastener(s) 12 (e.g., nut 12) and proximal receptacle 80 can be configured in a manner that adjusts the amount of suction-induced flow through the proximal receptacle. As another example, it is believed that the nut 12 and/or other suitable features (e.g., one or more clips, covers, or other suitable features) can be provided and/or sized to more fully obstruct (e.g., substantially obstruct or close) and/or cover the proximal receptacle 80.

In accordance with the fifth embodiment and as best understood with reference to FIGS. 27, 28, 30, and 31, the widths of the respective gaps between the fastener 12 (e.g., nut) and the edges of the tube 10 that define the proximal receptacle 80 can be smaller than depicted FIGS. 27, 28, 30, and 31, so that, for example, one or more of, or each of, the gap widths are less than about 3 millimeters, less than about 2 millimeters, less than about 1 millimeter, in a range of from about 3 millimeters to about 0.5 millimeters, in a range of from about 2 millimeters to about 0.5 millimeters, about 1 millimeter, or any subranges or values therebetween. Also, top and bottom corners of the nut 12 and receptacle 80 can be rounded in a complementary manner in an effort to provide smooth relative movement/engagement therebetween (see, e.g., FIGS. 32-34).

Figure 34:
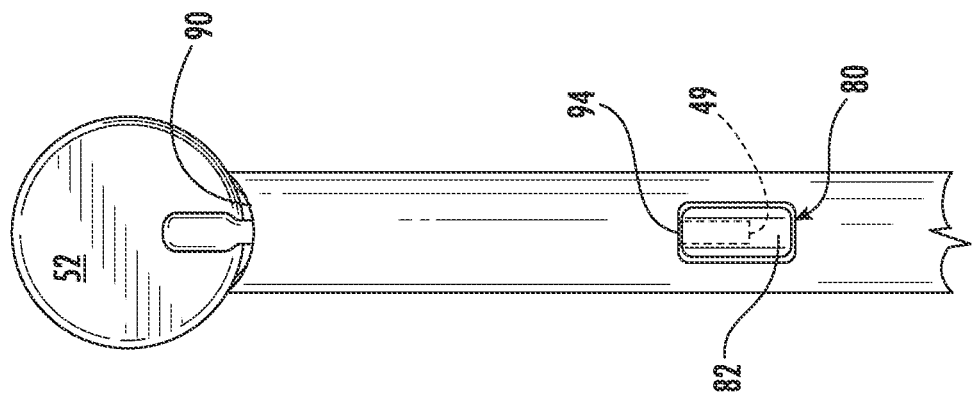
FIGS. 33 and 34 depict configurations/aspects of a method of mounting the mirror apparatus to a portion of the evacuation tip of FIGS. 21-25, wherein the nut is in the proximal position in FIG. 33, and the nut is in a distal position in FIG. 34, in accordance with an embodiment of this disclosure.
Figure 33:
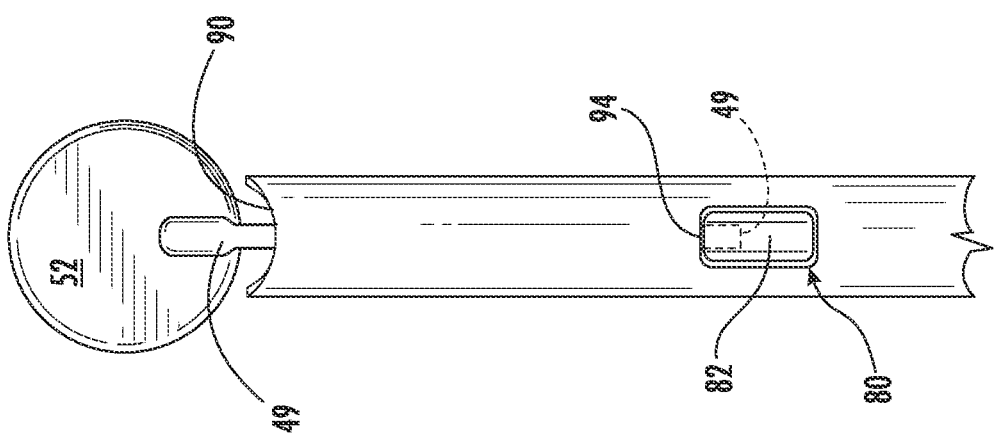
Figure 32:
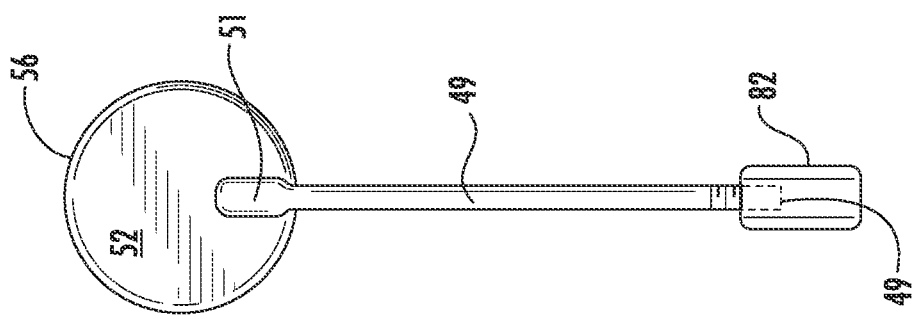
FIG. 32 is a rear elevation view of the mirror apparatus with a nut in a proximal position, in accordance with an embodiment of this disclosure.

An example of a method of removably mounting a mirror apparatus to the fifth embodiment tube 10 is described in the following with reference to the example depicted in FIGS. 32-34, in accordance with an embodiment of this disclosure. Referring to FIG. 32, at least one fastener 82 or other suitable fastening feature can be manually attached to the stem's proximal end portion. The fastener 82 can be, for example, a clip, or a nut having internal screw thread(s) configured to mesh with external screw thread(s) of the proximal end portion of the stem 49, and/or any other suitable fastening feature. The nut 82 can be, for example, a conventional square or hexagonal nut, a conventional coupling nut, and/or or any other suitable nut, or the like. In FIGS. 32-34, the proximal end portion of the stem 49, which is hidden from view within the nut 82, is schematically depicted with dashed lines. In the embodiment depicted in FIGS. 33 and 34, the outer overall dimensions of the nut 12 are about the same size as, or slightly smaller than, the corresponding cross-wise dimensions of the proximal receptacle 80.

FIGS. 32 and 33 can be characterized as depicting the nut 82 in a proximal position along the length of the stem 49. In contrast, FIG. 34 can be characterized as depicting the nut 82 in a distal position along the length of the stem 49. The nut 82 can be transitioned between the proximal and distal positions along the length of the stem 49 by way of manually implemented relative rotation between the nut and stem, and the associated interaction between the screw threads of the nut and stem.

With the nut 82 in its proximal position as shown in FIG. 32, initially the proximal end of the mirror apparatus' stem 49, with the nut 82 connected thereto, can be manually inserted through the tube's distal end opening 15 and/or the distal receptacle 42 and into the tube's interior space. Then, the stem 49 carrying the nut 82 can be manually guided farther through the distal end opening 15 and/or the distal receptacle 42 into the tube's interior space so that the proximal end of the stem 49, with the nut 82 thereon, travels in the tube interior space toward the tube's proximal end 12, or more specifically toward the tube's proximal receptacle 80.

The manually implemented relative movement between the tube 10 and mirror apparatus typically includes both lengthwise and lateral relative movement. The lengthwise relative movement typically includes causing the nut 82 on the stem's proximal end to become adjacent the proximal receptacle 80. The lateral relative movement typically includes causing a portion of the nut 82 on the stem's proximal end to extend outwardly through the proximal receptacle 80.

The relative movement typically continues until the predetermined portion of the nut 82 on the stem's proximal end extends outwardly through the proximal receptacle 80, a central portion of the stem 49 engages the rear interior surface of the tube 10, and optionally the rearward portion of the central portion of the stem 49 fits into the channel 92 (FIGS. 21 and 22).

Then, the mounting can be completed by manually transitioning the nut 82 from the proximal position (FIGS. 32 and 33) to the distal position (FIG. 34) so that an end of the nut firmly engages at least one predetermined edge 94 of the tube 10. In response to the transitioning of the nut 82 from the proximal position to the distal position, the stem 49 is drawn farther inwardly into the tube 10, so that relative movement between the mirror 54 and tabs 46 causes engagement therebetween.

The transitioning of the nut 82 from the proximal position to the distal position so that, for example, the mirror 54 and tabs 46 firmly engage one another can be facilitated by a user manually engaging the portion of the nut 82 that extends outwardly through the proximal receptacle 80 in a manner that causes the nut to rotate relative to the stem 49 and travel along the stem toward the head/mirror 54 of the mirror apparatus by way of the associated interaction between the screw threads of the nut and stem.

FIG. 34 depicts the mirror apparatus mounted to the tube 10 so that the nut 82 is in the distal position along the length of the stem 49, the predetermined end of the nut firmly engages the tube's intermediate edge 94 that at least partially defines the proximal receptacle 80, the mirror apparatus' head firmly engages the tube's distal end edge 90 that at least partially defines the distal mounting feature or hole 42, the distal end portion of the stem 49 extends through the distal receptacle 42, the rear sides of the engagement tabs 46 engage the mirror 54, a predetermined portion of the nut 82 extends outwardly through the proximal receptacle 80, the central portion of the stem 49 engages the rear interior surface of the tube 10, and optionally the rearward portion of the central portion of the stem 49 fits into the guideway or channel 92 (FIGS. 21 and 22).

Responsive to the predetermined end of the nut 82 firmly engaging the tube's intermediate edge 94 (and/or other suitable structure) and the mirror apparatus' head firmly engaging the tube's distal end edge 90 (and/or other suitable structure), a predetermined portion of the stem 49 is in tension and a predetermined portion of the tube 10 is in compression in a manner so that the mirror apparatus is fixedly (yet removably) connected to the tube 10. The mirror apparatus can be removed from the tube 10 by reversing the process of mounting the mirror apparatus to the tube.

Figure 35:
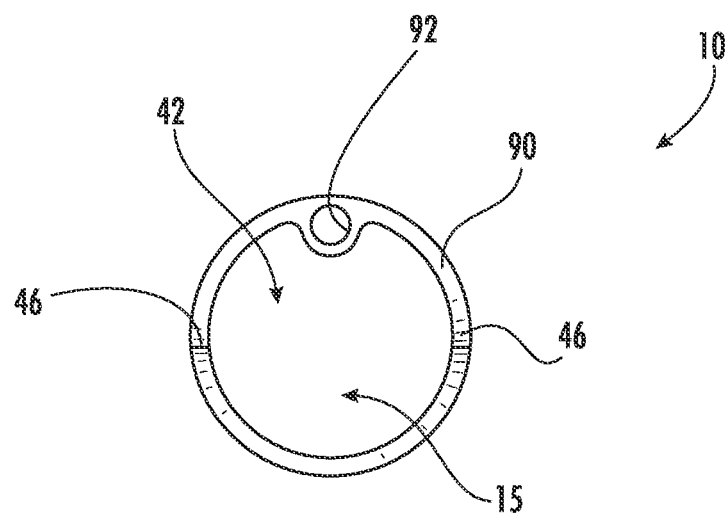
FIG. 35 is a top plan view of an evacuation tip in accordance with a sixth embodiment of this disclosure.

A sixth embodiment of this disclosure is like the fifth embodiment, except for variations noted and variations that will be apparent to those of ordinary skill in the art. Referring to the top plan view of FIG. 35, the elongate mounting guide or receptacle 92 of the sixth embodiment can be in the form of at least one passageway, tubular passageway, or tubular member 92 fixedly mounted to, or integrally formed with, the interior surface of the tubular body 10, or the like. The lengthwise axis of the tube 92 and its interior passageway can extend parallel to, and be offset from, the lengthwise axis of the outer tube 10. The tube 92 and/or passageway 92 can extend, for example, from one to the other of the receptacles 42, 80 along the length of the tube 10, or at least partially between the mounting hole or receptacles 42, 80.

In the sixth embodiment, the lengthwise dimension of the nut 12 is slightly smaller than the lengthwise dimension of the proximal receptacle 80, and the diameter or crosswise dimension of the fastener part or nut 12 is slightly larger than the crosswise dimension of the proximal receptacle 80. As a result of this relative configuration, the nut 12 can be manually laterally introduced from outside of the outer tube 10 partially into the proximal receptacle 80, until the inward movement of the nut is arrested when the nut engages lateral edges of the outer tube 10 that partially define the proximal receptacle. The nut 12 can be described as being in an inner configuration when the nut engages the lateral edges of the outer tube 10 that partially define the proximal receptacle, wherein the nut extends inwardly partially through the proximal receptacle 80.

In the sixth embodiment, when the nut 12 is in the inner configuration, the passageway through the nut 12 is at least about coaxial with the passageway 92. While the nut 12 is being manually held in the inner configuration, the proximal end of the stem 49 can be inserted through the guideway or passageway 92 and engaged against the nut. Then, while the nut 12 is being manually held in the inner configuration, the mirror apparatus can be rotated relative to the nut so that the nut becomes threadedly attached to the stem's proximal end portion and reaches the proximal position (see, e.g., FIG. 33).

In the sixth embodiment, the relative dimensions of respective features can be established so that, while the nut 12 is in the proximal position (see, e.g., FIG. 33) and is no longer manually held in the inner configuration, the mounting can be completed by manually transitioning the nut 82 from the proximal position (FIG. 33) to the distal position (FIG. 34) in the manner discussed above with reference to FIGS. 33 and 34.

Reiterating from above, it is within the scope of this disclosure for one or more of the terms "substantially," "about," "approximately," and/or the like, to qualify each of the adjectives and adverbs of the foregoing disclosure for the purpose of providing a broad disclosure. As an example, it is believed that those of ordinary skill in the art will readily understand that, in different implementations of the features of this disclosure, reasonably different engineering tolerances, precision, and/or accuracy may be applicable and suitable for obtaining the desired result. Accordingly, it is believed that those of ordinary skill will readily understand usage herein of the terms such as "substantially," "about," "approximately," and the like.

In the above description and/or figures, examples of embodiments have been disclosed. The present invention is not limited to such exemplary embodiments. Unless otherwise noted, specific terms have been used in a generic and descriptive sense and not for purposes of limitation. The use of the term "and/or" includes any and all combinations of one or more of the associated listed items.

The invention claimed is:

1. A dental evacuation tip configured to be connected to a mirror apparatus, the dental evacuation tip comprising:
a body defining:
first and second interior passageways each having a length extending along a length of the body, and
proximal and distal end openings to the first interior passageway that are spaced apart from one another along the length of the body, wherein the dental evacuation tip is configured to be operably connected to a vacuum pump so that the first interior passageway and the vacuum pump are in fluid communication via the proximal end opening;
the body comprising at least one sidewall extending around the first interior passageway, and a protrusion that extends inwardly into the first interior passageway, wherein:
the protrusion comprises opposite first and second surfaces,
the first surface is contiguous with the first interior passageway, and
the second surface is contiguous with the second interior passageway; and
at least a portion of the body being configured for use in releasably securing a mirror apparatus to the body so that, when the mirror apparatus is releasably secured to the body, simultaneously:
a portion of a stem of the mirror apparatus is positioned in the first interior passageway,
another portion of the stem is positioned in the second interior passageway, and
a reflective surface of a mirror of the mirror apparatus is proximate the distal end opening so that, when the vacuum pump is operably connected, the dental evacuation tip is configured to draw air and/or aerosols from a dental patient's mouth such that at least a portion of the air and/or aerosols contact and travel across the reflective surface of the mirror while the mirror apparatus is releasably secured to the body.

2. The dental evacuation tip according to claim 1, comprising a laterally open mounting hole in the at least one sidewall, wherein:
the laterally open mounting hole is positioned between, and spaced apart from each of, the proximal and distal end openings, and
the laterally open mounting hole is configured to provide access to an end portion of the stem when the mirror apparatus is releasably secured to the body.

3. The dental evacuation tip according to claim 2, comprising a fastening feature configured to engage a screw thread of the stem of the mirror apparatus when the mirror apparatus is releasably secured to the body, wherein:
the body comprises opposite proximal and distal ends;
the laterally open mounting hole is spaced apart from the proximal and distal ends of the body; and
the distal end opening of the first interior passageway is positioned at the distal end of the body.

4. The dental evacuation tip according to claim 1, comprising a laterally open mounting hole in the at least one sidewall, wherein the laterally open mounting hole in the at least one sidewall is configured to provide access to a portion of the stem when the mirror apparatus is releasably secured to the body.

5. The dental evacuation tip according to claim 4 in combination with the mirror apparatus, wherein simultaneously:
the mirror apparatus is releasably connected to the dental evacuation tip;
the portion of the stem of the mirror apparatus is positioned in the first interior passageway;
the reflective surface of the mirror of the mirror apparatus is proximate the distal end opening of the first interior passageway; and
the another portion of the stem is positioned in the second interior passageway.

6. The combination according to claim 5, comprising a fastening feature at least partially positioned in the laterally open mounting hole and engaged against a screw thread of the stem of the mirror apparatus to at least partially releasably secure the mirror apparatus to the body.

7. The combination according to claim 6, wherein a portion of the stem of the mirror apparatus is visible by way of the laterally open mounting hole in the at least one sidewall.

8. The combination according to claim 7, wherein the portion of the stem comprises:
a proximal end of the stem, and
a screw thread of the stem.

9. The combination according to claim 5 wherein:
a threaded portion of the stem of the mirror apparatus is opposite from the mirror of the mirror apparatus, and
the stem and the laterally open mounting hole are cooperatively configured so that part of the threaded portion is visible by way of the laterally open mounting hole.

10. The combination according to claim 5, comprising a nut threadedly engaged with a threaded portion of the stem, wherein a portion of the nut extends outwardly through the laterally open mounting hole.

11. The combination according to claim 5, comprising a fastening feature at least partially positioned in the laterally open mounting hole, and engaged against the stem of the mirror apparatus to at least partially releasably secure the mirror apparatus to the body.

12. The dental evacuation tip according to claim 1, wherein the protrusion protrudes inwardly into the first interior passageway in a plan view of the evacuation tip.

13. The dental evacuation tip according to claim 1, wherein the first surface of the protrusion defines a portion of the first interior passageway.

14. The dental evacuation tip according to claim 13, wherein the second surface of the protrusion defines the second interior passageway.

15. The dental evacuation tip according to claim 1, wherein:
the body comprises opposite proximal and distal ends;
the distal end opening of the first interior passageway is positioned at the distal end of the body; and
the body comprises opposite tabs positioned at the distal end of the body.

16. The dental evacuation tip according to claim 15, wherein the tabs are spaced apart from one another and configured to engage a head of the mirror apparatus when the mirror apparatus is releasably secured to the body.

17. The dental evacuation tip according to claim 15, wherein the distal end of the body comprises an edge that extends:
from a peak of a first of the tabs to a peak of a second of the tabs; and
partially along the length of the body.

18. The dental evacuation tip according to claim 17, wherein the edge is a first edge, and the distal end comprises a second edge that extends:
from the peak of the first tab to the peak of the second tab; and
partially along the length of the body.

19. A dental evacuation tip configured to be connected to a mirror apparatus, the dental evacuation tip comprising:
a body defining an interior passageway extending along a length of the body, and proximal and distal openings to the interior passageway that are spaced apart from one another along the length of the body; and
at least a portion of the body being configured for use in releasably securing a mirror apparatus to the body so that at least a portion of a stem of the mirror apparatus is positioned in the interior passageway and a reflective surface of a mirror of the mirror apparatus is proximate the distal opening;
wherein the dental evacuation tip is configured to be operably connected to a vacuum pump such that the dental evacuation tip and vacuum pump are in fluid communication via the proximal opening;
the at least the portion of the body is comprised of a receptacle defined by the body;
the receptacle is positioned between the proximal and distal openings;
the body comprises at least one sidewall extending around the interior passageway;
the receptacle comprises at least one hole that extends through the at least one sidewall;
the at least one hole comprises a first hole that extends through the at least one sidewall;
a second hole extends through the at least one sidewall and is open to the first hole, and the second hole is open at a distal end of the body;
a first tab portion of the at least one sidewall partially defines the first and second holes;
the first tab portion is flexibly configured to be deformed to at least temporarily enlarge the second hole for allowing at least a portion of the stem to be passed through the second hole and be received in the first hole;
the first tab portion is elastically configured to engage a backside of the mirror apparatus to at least partially releasably secure the mirror apparatus to the body;
a second tab portion of the at least one sidewall partially defines the first and second holes;
the second hole comprises a gap defined between the first and second tab portions;
the second tab portion is flexibly configured to be deformed to at least temporarily enlarge the second hole for allowing the stem to be passed through the second hole and be received in the first hole; and
the second tab portion is elastically configured to engage the backside of the mirror apparatus to at least partially releasably secure the mirror apparatus to the body.

20. The dental evacuation tip according to claim 19, wherein, when the vacuum pump is operably connected, the dental evacuation tip is configured to draw air and/or aerosols from a dental patient's mouth such that at least a portion of the air and/or aerosols contact and travel across the reflective surface of the mirror while the mirror apparatus is releasably secured to the body.

\* \* \* \* \*